US008211837B2

(12) United States Patent
Weerasooriya et al.

(10) Patent No.: US 8,211,837 B2
(45) Date of Patent: Jul. 3, 2012

(54) METHOD OF MANUFACTURE AND USE OF LARGE HYDROPHOBE ETHER SULFATE SURFACTANTS IN ENHANCED OIL RECOVERY (EOR) APPLICATIONS

(75) Inventors: Upali P. Weerasooriya, Austin, TX (US); Gary A. Pope, Cedar Park, TX (US); Quoc P. Nguyen, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 12/887,858

(22) Filed: Sep. 22, 2010

(65) Prior Publication Data

US 2011/0071057 A1 Mar. 24, 2011

Related U.S. Application Data

(60) Provisional application No. 61/244,795, filed on Sep. 22, 2009.

(51) Int. Cl.
*C09K 8/584* (2006.01)
*C07C 305/00* (2006.01)

(52) U.S. Cl. .......... 507/259; 507/253; 507/254; 558/20; 558/44

(58) Field of Classification Search .................. 507/259, 507/253, 254; 558/20, 44
See application file for complete search history.

(56) References Cited

U.S. PATENT DOCUMENTS

| 4,011,273 | A | 3/1977 | Abend et al. |
| 5,777,183 | A | 7/1998 | Mueller et al. |
| 6,008,181 | A | 12/1999 | Cripe et al. |
| 7,074,753 | B2 | 7/2006 | Gallotti et al. |
| 7,076,753 | B2 | 7/2006 | Cerny et al. |
| 7,119,125 | B1 | 10/2006 | O'Lenick, Jr. et al. |
| 2008/0200565 | A1 | 8/2008 | Harwell et al. |
| 2008/0217064 | A1 | 9/2008 | Stolan et al. |

OTHER PUBLICATIONS

Adkins, S., et al., "A New Process for Manufacturing and Stablizing High-Performance EOR Surfactants at Low Cost for High-Temperature, High Salinity Oil Reservoirs." Paper SPE 129923, presented at the 2010 SPE Improved Oil Recovery Symposium, Tulsa, Oklahoma, Apr. 24-28, 2010; US.
Flaaten, A., et al., "A Systemic Laboratory Approach to Low-Cost, High-Performance Chemical Flooding," Paper SPE 113469. presented at the 2008 SPE/DOE Improved Oil Recovery Symposium, Tulsa, Oklahoma, Apr. 20-23, 2008. Society of Petroleum Engineers, US.
Flaaten, A., "Experimental Study of Microemulsion Characterization and Optimization in Enhanced Oil Recovery: A Design Approach for Reservoirs with High Salinity and Hardness," Thesis, The University of Texas at Austin (Dec. 2007); US.
Healy, R.N., et al. "Multiphase Microemulsion Systems," Society of Petroleum Engineers Journal, 16(3), Jun. 1976; pp. 147-160; Society of Petroleum Engineers: US.
Huh, C., "Interfacial Tensions and Solubilizing Ability of a Microemulsion Phase That Coexists With Oil and Brine," Journal of Colloid and Interface Science, 71(2), Sep. 1979; pp. 408-426, Academic Press, Inc.; US.
Jackson, A.C., "Experimental Study of the Benefits of Sodium Carbonate on Surfactants for EOR," Thesis, The University of Texas at Austin (Dec. 2006); US.
Levitt, D.B., et al., "Identification and Evaluation of High-Performance EOR Surfactants," Paper SPE 100089, presented at the SPE/DOE Improved Oil Recovery Symposium, Tulsa, Oklahoma, Apr. 22-26, 2006; Society of Petroleum Engineers Reservoir Evaluation & Engineering: Apr. 2009, US.
Liu, Q., et al., "Surfactant Enhanced Alkaline Flooding for Western Canadian heavy oil recovery;" Colloids and Surfaces A: Physicochemical and Engineering Aspects, 293(1-3); Feb. 2007; pp. 63-71; Elsevier Sciences; NL.
O'Lenick Jr., A.J., "Guerbet Chemistry," Journal of Surfactants and Detergents, vol. 4, No. 3; Jul. 2001; pp. 311-315; American Oil Chemist Society; Urbana, IL; US.
O'Lenick Jr., et al., "Effects of Branching Upon Some Surfactant Properties of Sulfated Alcohols," Journal of the American Oil Chemists' Society, vol. 73, No. 7, no month, 1996: pp. 935-937; American Oil Chemist Society; Urbana, IL; US.
Talley, L.D, "Hydrolytic Stability of Alkylethoxy Sulfates," SPE Reservoir Engineering. 3(1); Feb. 1988; pp. 235-242; Society of Petroleum Engineers; US.
Winsor, Von P.A., "Solvent Properties of Amphiphilic Compounds," Butterworths Scientific Publ. Ltd. (London 1954).
Yang, H., et al., "Low-Cost, High Performance Chemicals for Enhanced Recovery," Paper SPE 129978, presented at the 2010 SPE Improved Oil Recovery Symposium, Tulsa, Oklahoma, Apr. 24-28, 2010; US.
Zhao, Ping, "Development of High-Performance Surfactants for Difficult Oils," Thesis, The University of Texas at Austin; Dec. 2007; US.
Varadaraj. ET., et al.; "Fundamental interfacial properties of alkyl-branched sulfate and ethoxy sulfate surfactants derived from Guerbet Alcohols. 1, Surface and Instantaneous Interfacial Tensions"; The Journal of Physical Chemistry, vol. 95, No. 4; Feb. 28, 1991; American Chemical Society; US.
Minana-Perez, et al.; "Solubilization of Polar Oils with Extended Surfactants"; Colloids and Surfaces; A: Physiocochemical and Engineering Aspects 100; pp. 217-224; no month, 1995; Elsevier Sciences B.V., NL.

(Continued)

*Primary Examiner* — Timothy J. Kugel
(74) *Attorney, Agent, or Firm* — Kelly Kordzik; Matheson Keys Garsson & Kordzik PLLC

(57) ABSTRACT

The present invention describes the method of making anionic ether sulfate surfactants by alkoxylation of a GA using PO and/or EO followed by a sulfation reaction. The GA of the present invention is made by a facile and inexpensive method that involves high temperature base catalyzed dimerization of a linear alcohol. The ether sulfate surfactants of the present invention find uses in EOR applications where it is used for solubilization and mobilization of oil and for environmental cleanup.

51 Claims, 9 Drawing Sheets

OTHER PUBLICATIONS

Jamaloei, Benyamin Yadali; "Insight into the Chemistry of Surfactant-Based Enhanced Oil Recovery Process"; Recent Patents on Chemical Engineering 2(1); pp. 1-10; Jan. 31, 2009; Bentham Science Publishers Ltd.; UAE.

Korean International Searching Authority; International Search Report & Written Opinion for PCT/US2010/049784; May 23, 2011; Korean Patent Office; KR.

Patent Cooperation Treaty; International Search Report and Written Opinion; PCT/US2010/049784; May 23,2011, 12 pages.

Patent Cooperation Treaty; International Preliminary Report on Patentability; PCT/US2010/049784: Apr. 5, 2012, 8 pages.

TABLE 1A

0.3% C32-7PO-6EO sulfate, 0.3% C20-24 IOS @ 85C (50% Oil Scan)

| Hydrocarbon | Crude Oil | | | Hydrocarbon Density | 0.84 | g/cc | Typical Hydrocarbon Densities: | |
|---|---|---|---|---|---|---|---|---|
| Surfactant | C-32-7PO-6EO Sulfate | | | Total Surfactant Conc. | 0.6 | wt % | Octane | 0.702 |
| Co-Surfactant(t) | C20-24 IOS | | | Total Alcohol Conc. | 0 | wt % | Decane | 0.73 |
| Co-Solvent | | | | Polymer Conc. | 0 | - | | |
| Surfactant Conc. | 0.3 | wt % | | Na2CO3 Conc. | 0 | wt % | Mixed: | #N/A |
| Co-surf(t) Conc. | 0.3 | wt % | | WOR | 1 | - | | |
| IBA-80-1 Conc. | 0 | wt % | | | | | | Extended scan |
| TDA-30 Sulfate | | wt % | | Temperature | 85 | Celsius | | |
| NaCl:CaCl Ratio | | | | Tube Size | 5 | mL | | |

| Salinity (wt% Na2CO3) | (ppm Na2CO3) | Aqueous Level | Hydrocarbon Level | Top of emulsion | Top Interface | Bottom Interface | Bottom of emulsion | Type | Volume of Oil Solubilized (cc) | Volume of Water Solubilized (cc) | Oil Sol. Ratio (cc/cc) | Water Sol. Ratio (cc/cc) | HC Sol. (mg/L) | Volume Fraction of Oil ($V_o$) | Volume Fraction of Microemulsion ($V_{me}$) | Volume Fraction of Water ($V_w$) | $V_o + V_{me}$ | Notes |
|---|---|---|---|---|---|---|---|---|---|---|---|---|---|---|---|---|---|---|
| | | 9/30/2009 | 456 days | | | | | | | | | | | | | | | |
| 0.00% | 0 | 2.80 | 2.80 | | | | | 1 | 0.00 | | 0.0 | | 0 | 0.507 | 0.493 | 0.000 | 0.493 | |
| 0.50% | 5000 | 2.80 | 2.80 | | | | | 1 | 0.04 | | 3.2 | | 15,781 | 0.478 | 0.522 | 0.000 | 0.522 | |
| 1.00% | 10000 | 2.80 | 2.80 | | | | | 1 | 0.08 | | 6.3 | | 30,625 | 0.466 | 0.532 | 0.000 | 0.532 | |
| 1.50% | 15000 | 2.80 | 2.80 | | | | | 1 | 0.07 | | 5.7 | | 27,736 | 0.483 | 0.517 | 0.000 | 0.517 | |
| 2.00% | 20000 | 2.80 | 2.80 | | | | | 1 | 0.10 | | 7.9 | | 38,182 | 0.463 | 0.537 | 0.000 | 0.537 | |
| 2.50% | 25000 | 2.80 | 2.80 | | 2.72 | | | III | 0.18 | | 14.3 | | 68,318 | 0.444 | 0.556 | 0.000 | 0.556 | |
| 3.00% | 30000 | 2.80 | 2.80 | | 2.70 | 3.10 | | III | 0.20 | 0.20 | 15.9 | 15.9 | 420,000 | 0.439 | 0.098 | 0.463 | 0.561 | |
| 3.50% | 35000 | 2.85 | 2.80 | | 2.81 | 3.00 | | III | 0.14 | 0.05 | 11.4 | 4.1 | 616,847 | 0.466 | 0.046 | 0.488 | 0.534 | |
| 4.00% | 40000 | 2.80 | 2.80 | | | 2.66 | | II | | 0.05 | | 4.5 | NA | 0 | 0.502 | 0.498 | 1.000 | |
| 4.50% | 45000 | 2.80 | 2.80 | | | | Gel | II | | 0.00 | | 0.0 | NA | 0 | 0.460 | 0.540 | 1.000 | |

| Salinity (wt% Na2CO3) | (ppm Na2CO3) | Aqueous Level | Hydrocarbon Level | Top of emulsion | Top Interface | Bottom Interface | Bottom of emulsion | Type | Volume of Oil Solubilized (cc) | Volume of Water Solubilized (cc) | Oil Sol. Ratio (cc/cc) | Water Sol. Ratio (cc/cc) | HC Sol. (mg/L) | Volume Fraction of Oil ($V_o$) | Volume Fraction of Microemulsion ($V_{me}$) | Volume Fraction of Water ($V_w$) | $V_o + V_{me}$ | Notes |
|---|---|---|---|---|---|---|---|---|---|---|---|---|---|---|---|---|---|---|
| | | 5/8/2008 | 21 days | | | | | | | | | | | | | | | |
| 0.00% | 0 | 2.80 | 2.80 | | 2.97 | | | 1 | 0.01 | | 0.6 | | 4,135 | 0.505 | 0.495 | 0.000 | 0.495 | |
| 0.50% | 5000 | 2.80 | 2.80 | | 2.87 | | | 1 | 0.03 | | 2.4 | | 11,831 | 0.480 | 0.520 | 0.000 | 0.520 | |
| 1.00% | 10000 | 2.80 | 2.80 | | 2.81 | | | 1 | 0.09 | | 7.1 | | 34,521 | 0.466 | 0.534 | 0.000 | 0.534 | |
| 1.50% | 15000 | 2.80 | 2.80 | | 2.86 | | | 1 | 0.07 | | 5.7 | | 27,736 | 0.483 | 0.517 | 0.000 | 0.517 | |
| 2.00% | 20000 | 2.80 | 2.80 | | 2.80 | | | 1 | 0.10 | | 7.9 | | 38,182 | 0.463 | 0.537 | 0.000 | 0.537 | |
| 2.50% | 25000 | 2.80 | 2.80 | | 2.70 | 2.88 | | III | 0.20 | -0.02 | 15.9 | -1.6 | 933,333 | 0.439 | 0.044 | 0.517 | 0.561 | |
| 3.00% | 30000 | 2.80 | 2.80 | | 0.60 | 4.10 | | III | 1.98 | 1.20 | 157.9 | 95.2 | 524,013 | 0.002 | 0.776 | 0.220 | 0.699 | |
| 3.50% | 35000 | 2.85 | 2.80 | | 2.80 | 3.00 | | III | 0.15 | 0.05 | 12.2 | 4.1 | 830,000 | 0.463 | 0.049 | 0.488 | 0.537 | |
| 4.00% | 40000 | 2.80 | 2.80 | | | | | 1 | | | | | 0 | -0.220 | 1.220 | 0.000 | 1.220 | |
| 4.50% | 45000 | 2.81 | 2.80 | | | 2.65 | | II | -0.01 | | -0.8 | | NA | 0 | 0.488 | 0.512 | 1.000 | |

FIG. 3

TABLE 1B

FIG. 4

METHOD OF MANUFACTURE AND USE OF LARGE HYDROPHOBE ETHER SULFATE SURFACTANTS IN ENHANCED OIL RECOVERY (EOR) APPLICATIONS

CROSS-REFERENCE TO RELATED APPLICATIONS

This Application for Patent claims the benefit of priority from U.S. Provisional Patent Application Ser. No. 61/244,795, filed Sep. 22, 2009, entitled "Method of Manufacture And Use Of Large Hydrophobe Ether Sulfate Surfactants In Enhanced Oil Recovery (EOR) Application," which provisional patent application is commonly assigned to the assignee of the present invention, and which disclosure is considered part of and is incorporated by reference in its entirety in the disclosure of this application.

TECHNICAL FIELD OF THE INVENTION

The present invention relates in general to the field of oil recovery, and more particularly, to a method of transforming Guerbet Alcohols (GA) to ether sulfates and the use of the large hydrophobe anionic ether sulfates manufactures by this method for EOR applications.

BACKGROUND OF THE INVENTION

Without limiting the scope of the invention, its background is described in connection with methods of manufacture and use of GA and related compounds including surfactant compositions in oil recovery.

U.S. Pat. No. 4,011,273 issued to Abend and Leenders (1977) describes the production of Guerbet alcohols by the condensation of alcohols in the presence of a catalyst and an alkali consisting of utilizing from 0.05 to 3.0 gm per mol of total alcohol of an insoluble lead salt of an oxyacid of a group IV element having a molecular weight greater than 27, such as oxyacids selected from the group consisting of the silicate, the titanate, the zirconate, the germanate and the hafnate, as said catalyst.

U.S. Pat. No. 7,119,125 issued to O'Lenick et al. (2006) relates to specific compositions made by the sulfation of alkoxylated crude Guerbet alcohol mixtures that contain between 15% and 50% lower molecular weight alkoxylated alcohols. According to the '125 patent the lower molecular weight alcohols are the raw material alcohols used to make the Guerbet. Sulfated compositions made from this specific bi-modal distribution have unique emulsification properties and experience minimal chromatographic separation when used in downhole applications.

United States Patent Application No. 20080217064 (Stoian and Smith, 2008) discloses a drilling fluid comprising: a non-ionic surfactant including at least one of a branched alcohol ethoxylate and a capped alcohol ethoxylate, a detergent builder and a viscosifier. The non-ionic surfactant includes alkyl polyethylene glycol ethers based on C10-Guerbet alcohol and ethylene oxide.

SUMMARY OF THE INVENTION

The present invention describes a facile and inexpensive manufacturing method for anionic ether sulfate surfactants from high molecular weight highly and precisely branched GA. The ether sulfates manufactured are used for solubilization and mobilization of oil in EOR applications.

An alcohol dimerization process known as the Guerbet reaction is used to create large alcohol structures for the production of the corresponding alkoxy sulfate surfactants. In the alcohol industry, Guerbet (dimer) alcohols are considered the "gold" standard for large, branched alcohols. These Guerbet alcohols tend to be more expensive than other alcohols when produced in high purity for various industrial applications. The high cost is mainly due to driving the reaction to completion and/or stripping-off of the unreacted monomer alcohol to produce high purity. However, inexpensive Guerbet alcohols (GA) can be prepared by aiming for less than quantitative conversion during the alcohol dimerization process. The resultant blend (such as, for example, 85-95% GA and 5-15% monomer alcohol) is subsequently used in the alkoxylation process to add propylene oxide (PO) and/or ethylene oxide (EO), followed by sulfation. Through the use of this new Guerbet process, these surfactants can be manufactured at low cost when made as sulfates as opposed to sulfonates. For example, a C32 GA can be produced from a C16 alcohol. These and other sulfate surfactants can be stabilized at high temperature with alkali. This is a surprising discovery that greatly increases the availability of low-cost, high performance surfactants for high temperature reservoirs.

In general, in one aspect, the invention features a method that includes dimerizing a linear alcohol at a high temperature in the presence of a base to form a Guerbet Alcohol. The step of dimerizing yields a blend comprising between 85 wt % and 95 wt % of the Guerbet Alcohol and between 5 wt % and 15% wt % of the unreacted linear alcohol. The method further includes converting the blend to a surfactant.

Implementations of the invention can include one or more of the following features:

The base can be NaOH, KOH, or both.

The base can be a catalyst for the step of dimerizing.

The Guerbet Alcohol can be a highly branched Alcohol hydrophobe.

The blend can include between 85 wt % and 95 wt % of the Guerbet Alcohol and between 5 wt % and 15 wt % of the unreacted linear alcohol.

The linear alcohol can have a general formula $C_nH_{2n-1}OH$, wherein n is an integer between 6 and 22, inclusive.

The linear alcohol can have a formula $C_{16}H_{33}OH$.

The Guerbet Alcohol can be branched at about the midpoint of the carbon chain.

The dimerization can be carried out a temperature range of about 175° C. to about 275° C.

The dimerization is carried out at a temperature of 175° C., 190° C., 200° C., 220° C., 230° C., 240° C., 250° C., or 275° C.

The dimerization can be carried out at 230° C.

The step of converting the blend to a surfactant can include an alkoxylation process. The alkoxylation process can add an alkylene oxide to the Guerbet Alcohol. The alkylene oxide can be propylene oxide, ethylene oxide, or a combination thereof. The step of converting the alkoxylated blend to a surfactant can include a sulfation process.

The surfactant can have a chemical formula of $C_nH_{2n+1}O-PO_x-EO_y-SO_3^-$. In this formula, n can be an integer between 12 and 44, inclusive; x can be an integer between 0 and 50, inclusive; and y can be an integer between 0 and 100, inclusive.

Either or both of x and y can be a non-zero integer.

The step of converting the blend to a surfactant can include a sulfation process.

The surfactant can be an anionic surfactant.

The method can further include utilizing the surfactant in a surfactant based application. The surfactant based application can be an application for enhanced oil recovery (EOR) or an application for environmental ground water cleanup.

The surfactant can be an anionic ether sulfate surfactant. The Guerbet Alcohol can be formed in the step of dimerizing. The Guerbet Alcohol can have a general formula of $C_nH_{2n+1}OH$. During the step of converting, the Guerbet Alcohol can be alkoxylated to form an alkoxylated Guerbet Alcohol. During the step of converting, the alkoxylated Guerbet Alcohol can be sulfated to produce the anionic ether sulfate surfactant.

The method can further include using the anionic ether sulfate surfactant in a surfactant based application. The surfactant based application can be an enhanced oil recovery (EOR) application or an environmental ground water cleanup.

The anionic ether sulfate surfactant can have a formula of $C_{32}H_{65}O-PO_7-EO_6-SO_3^-$.

In the general formula for the surfactant ($C_nH_{2n+1}O-PO_x-EO_y-SO_3^-$), n can be 12, 15, 18, 20, 22, 25, 28, 30, 35, 38, 40, 42, or 44; x can be 0, 2, 5, 8, 10, 12, 14, 16, 18, 20, 30, 40, or 50; and y can be 0, 5, 10, 15, 20, 25, 30, 35, 40, 45, 50, 55, 60, 65, 70, 80, 90, or 100.

In general, in another aspect, the invention features composition that includes an anionic ether sulfate surfactant having a formula of $C_nH_{2n+1}O-PO_x-EO_y-SO_3^-$. In this formula, n is an integer between 12 and 44, inclusive; x is an integer between 0 and 50, inclusive, and y is an integer between 0 and 100, inclusive.

Implementations of the invention can include one or more of the following features:

The anionic ether sulfate surfactant can be produced by a process that includes dimerizing a linear alcohol at a high temperature in the presence of a base to form a Guerbet Alcohol. This dimerizing process can yield a blend that includes between 85 wt % and 95 wt % of the Guerbet Alcohol and between 5 wt % and 15 wt % of the unreacted linear alcohol. The process to produce the anionic ether sulfate surfactant can further include performing an alkoxylation process to add an alkylene oxide to the Guerbet Alcohol. The alkylene oxide can be propylene oxide, ethylene oxide, or a combination thereof. The process to produce the anionic ether sulfate surfactant can further include performing a sulfation process to the alkoxylated Guerbet Alcohol to form the anionic ether sulfate surfactant.

The composition can be operable for use in an enhanced oil recovery (EOR) application.

The composition can be operable for use in an environmental ground water cleanup application.

The anionic ether sulfate surfactant can include $C_{32}H_{65}O-PO_7-EO_6-SO_3^-$ and $C_{16-18}-H_{33-37}-O-PO_7-EO_6-SO_3^-$.

The anionic ether sulfate surfactant can include 85 wt % of $C_{32}H_{65}O-PO_7-EO_6-SO_3^-$ and 15 wt % $C_{16-18}-H_{33-37}-O-PO_7-EO_6-SO_3^-$.

In the formula of $C_nH_{2n+1}O-PO_x-EO_y-SO_3^-$ of the composition, n can be 12, 15, 18, 20, 22, 25, 28, 30, 35, 38, 40, 42, or 44; x can be 0, 2, 5, 8, 10, 12, 14, 16, 18, 20, 30, 40, or 50; and y can be 0, 5, 10, 15, 20, 25, 30, 35, 40, 45, 50, 55, 60, 65, 70, 80, 90, or 100.

Either or both of x and y can be a non-zero integer.

The composition can further include an alkalinity generating agent and a solvent. The anionic ether sulfate surfactant and the alkalinity generating agent can be dissolved in the solvent.

The composition can further include an additional anionic surfactant that is a sulfate, sulfonate, carboxylate anion based surfactant, ether sulfate, ethoxy sulfate, propoxy sulfate, $C_{32}H_{65}O-PO_7-EO_6-SO_3^-$, $C_{12-15}$-3EO sulfate, $C_{12-15}$-12EO sulfate, $C_{16-17}$-7PO sulfate, $C_{13}$-7PO sulfate, $C_{16-18}$-7PO-5EO sulfate, $C_{20}$-7PO-10EO sulfate, perfluorooctanoate (PFOA or PFO), perfluorooctanesulfonate (PFOS), sodium dodecyl sulfate (SDS), ammonium lauryl sulfate, alkyl sulfate salt, sodium lauryl ether sulfate (SLES), alkyl benzene sulfonate, soap, fatty acid salt, or a combination thereof.

The alkalinity generating agent can be alkali earth metal hydroxides, NaOH, KOH, LiOH, ammonia, $Na_2CO_3$, $NaHCO_3$, Na-metaborate, sodium silicate, sodium orthosilicate, $EDTANa_4$, polycarboxylate, or a combination thereof.

The solvent can be water, a polymer containing solution, or a combination thereof. The water can be hard brine or hard water.

The composition can be used alone or in an alkaline-surfactant-polymer formulation for an enhanced oil recovery (EOR) application.

The composition can include between 0.01 wt % and 5 wt % of the alkalinity generating agent.

In general, in another aspect, the invention features a method of using an anionic ether sulfate surfactant formulation for enhanced oil recovery from a hydrocarbon bearing formation. The method includes injecting an anionic ether sulfate surfactant composition into the hydrocarbon bearing formation at a temperature between 25° C. to 120° C. The anionic ether sulfate composition includes an anionic ether sulfate having a chemical formula $C_nH_{2n+1}O-PO_x-EO_y-SO_3^-$. In this chemical formula n is an integer between 12 and 44, inclusive; x is an integer between 0 and 50, inclusive; and y is an integer between 0 and 100, inclusive. The anionic ether sulfate composition is injected either alone or as an alkaline-surfactant-polymer formulation (ASP). The method further includes injecting a polymer push solution to recover oil.

Implementations of the invention can include one or more of the following features:

The anionic ether sulfate surfactant composition can further include water and an alkalinity generating agent. The water can be either hard water or hard brine.

The anionic ether sulfate surfactant composition can include at least 0.1 wt % of the alkalinity generating agent.

The anionic ether sulfate surfactant composition can further include an additional anionic surfactant that is a sulfate, sulfonate, carboxylate anion based surfactant, ether sulfate, ethoxy sulfate, propoxy sulfate, $C_{32}H_{65}O-PO_7-EO_6-SO_3^-$, $C_{12-15}$-3EO sulfate, $C_{12-15}$-12EO sulfate, $C_{16-17}$-7PO sulfate, $C_{13}$-7PO sulfate, $C_{16-18}$-7PO-5EO sulfate, $C_{20}$-7PO-10EO sulfate, perfluorooctanoate (PFOA or PFO), perfluorooctanesulfonate (PFOS), sodium dodecyl sulfate (SDS), ammonium lauryl sulfate, alkyl sulfate salt, sodium lauryl ether sulfate (SLES), alkyl benzene sulfonate, soap, fatty acid salt, or a combination thereof.

The alkalinity generating agent can be alkali earth metal hydroxides, NaOH, KOH, LiOH, ammonia, $Na_2CO_3$, $NaHCO_3$, Na-metaborate, sodium silicate, sodium orthosilicate, $EDTANa_4$, polycarboxylate, or a combination thereof.

BRIEF DESCRIPTION OF THE DRAWINGS

For a more complete understanding of the features and advantages of the present invention, reference is now made to the detailed description of the invention along with the accompanying figures and in which:

FIG. 3 is a table (Table 1A) that shows phase behavior data recording sheets corresponding to the plot shown in FIG. 2A.

FIG. 4 is a table (Table 1B) that shows phase behavior data recording sheets corresponding to the plot shown in FIG. 2B.

DETAILED DESCRIPTION OF THE INVENTION

Figure 1:
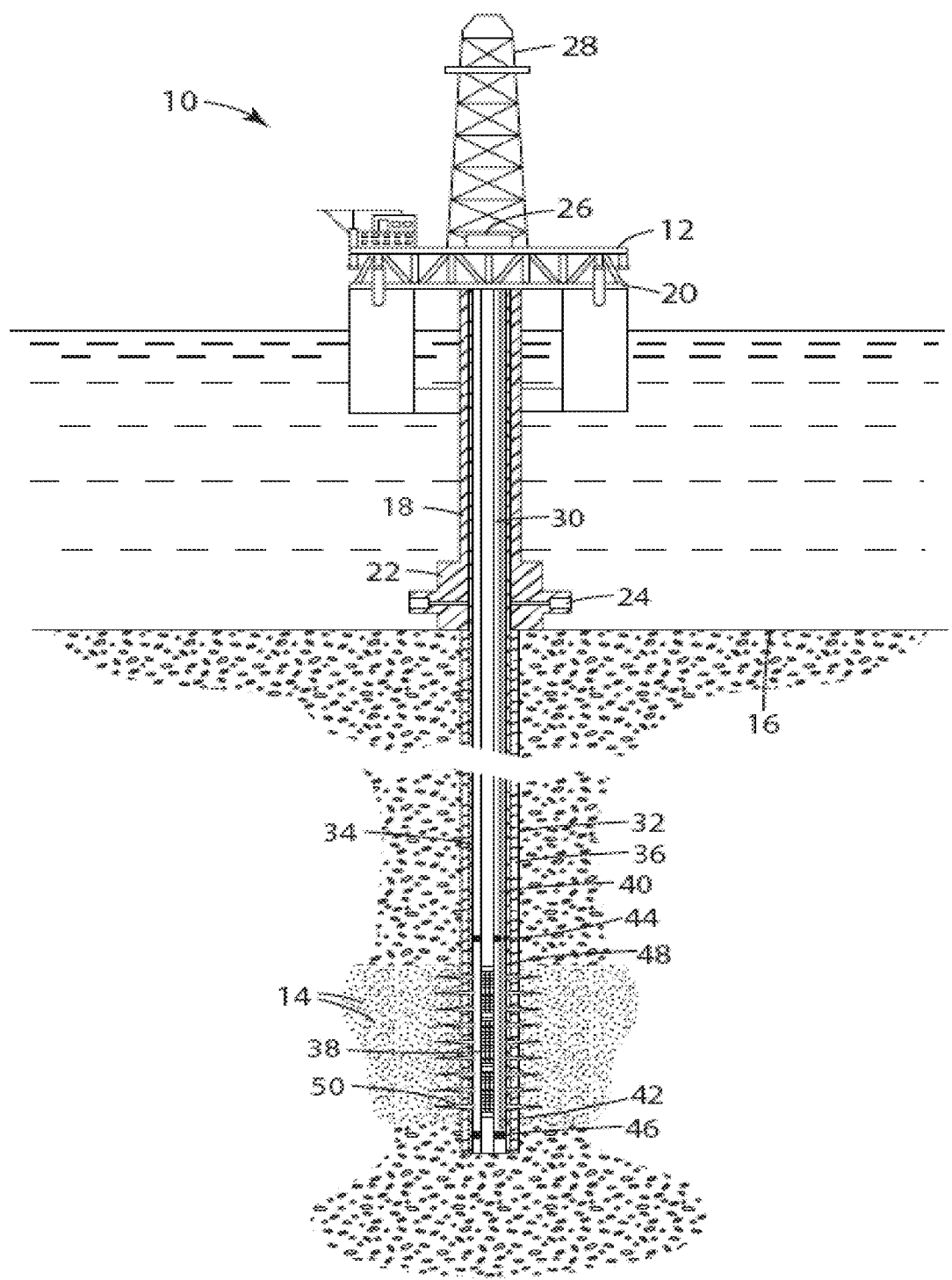
FIG. 1 is a schematic illustration of an offshore oil platform with facilities for injecting chemical solutions into the reservoir for the purpose of flooding the reservoir to enhance the oil recovery according to some embodiments of the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Guerbet Alcohols are made by base catalyzed, high temperature dimerization of an alcohol. These molecules are highly branched and offer a way to achieve high molecular weight, highly and precisely branched alcohols (large hydrophobes) that can be transformed into ether sulfates. Phase behavior studies conducted by the present inventors have shown that such surfactants have exaggerated hydrophobicity and are capable of solubilizing higher amounts of crude oil. An inherent disadvantage of these Guerbet alcohol derivatives is the high cost of the Guerbet alcohol (GA). This is mainly attributable to the high purity of the alcohol which necessitates the driving of the reaction to near completion.

In order to make these molecules cost competitive, the present inventors claim a lower cost Guerbet alcohol where in the Guerbet reaction can be carried out to about 85-95% level leaving about 5-15% of "monomer" alcohol in the Guerbet alcohol product. Similar structures can be achieved by dimerizing Alfa Olefin to the same degree followed by Hydroformylation. The next two steps are carried out on this inexpensive GA to generate the Alkoxy or Ether Sulfate (propoxy and/or ethoxy). The Guerbet alcohol Ether sulfate will provide high oil solubilization whereas the Monomer Ether sulfate will function as a hydrophilic co-surfactant assisting in the aqueous stability (solubility) of the Guerbet surfactant. This minimizes the need for using co-solvents in the surfactant formulation.

Guerbet reaction is a method for making highly branched, large hydrophobe alcohols. Alternatively, similar large hydrophobe alcohols can be made by dimerization of alfa olefins followed by hydroformylation. Consequently, the present inventors have a new array of high molecular weight branched anionic surfactants that can find applications in reservoir EOR applications or environmental cleanup work.

Guerbet reaction dimerizes linear alcohol using base catalysis at high temperatures (like 230° C.) to produce near mid-point branching (O'Lenick Jr. 2001)—most feasible way to extra-large hydrophobes. Guerbet alcohols (GA) are considered "gold" standard for highly branched alcohols which are low melting liquids. There is a need for large hydrophobes with branching for heavy oil mobilization. For instance, when the equivalent alkane carbon number (EACN) of a crude oil is higher than about 12, surfactants with very large hydrophobes and branched structures are required to obtain ultra-low interfacial tensions and low microemulsion viscosities (Liu 2007) and this is even more difficult to achieve at high temperature and/or high salinity and hardness. The cost of these very large hydrophobe surfactants can be prohibitive. However, inexpensive Guerbet alcohols (GA) can be prepared by aiming for less than quantitative conversion during the alcohol dimerization process.

The present invention describes an inexpensive method to create large hydrophobes from smaller linear alcohols using the Guerbet reaction (example: $C_{32}$ alcohol formed from $2C_{16}$).

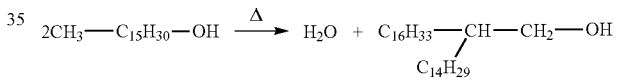

GA can be alkoxylated using EO and/or PO and then sulfated to produce anionic surfactants. (O'Lenick, Jr. 1996) Guerbet surfactants can be tailored to fit EOR needs based on the number of PO and number of EO groups. For example,

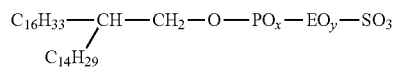

Sulfation of a hydrophobe is the simplest and most versatile method of making anionic surfactants. Consequently, a new array of anionic surfactants that can find applications in high temperature reservoir EOR applications becomes available. Sulfation, by virtue of its simplicity, is the least expensive method of producing an anionic surfactant. The discovery of how to vastly enhance ES stability at elevated temperatures broadens the field of low cost anionic EOR Surfactants significantly.

The present invention can be used in any application (e.g., surface or near-surface treatments, downhole or for Enhanced Oil Recovery) that involves high temperature conditions, such as, environmental cleanup of ground water contaminated by oils and other organic solvents.

In addition to being less expensive, mixtures of GA and monomer alcohol (such as 85%-95% GA and 5-15% monomer alcohol) also appear to be more effective when made into anionic surfactants for enhanced oil recovery than higher purity GA products that require more reactor time and higher cost to manufacture. The un-reacted alcohol monomer subsequently ends up as a co-surfactant during the surfactant manufacturing process with the mixture of surfactants being more effective than the pure surfactant. When higher purity GA are used to produce the alkoxy sulfates, the final surfactant molecules are still of reasonable cost due to the high molecular weight of the sulfate surfactant. For example, in Guerbet C32-7PO-10EO sulfate the GA is only 33% of the entire surfactant molecule based on weight. Through the use of the Guerbet process disclosed herein, these surfactants can be manufactured at low cost when made as sulfates as opposed to sulfonates. The use of a GA is a highly feasible way to produce very large hydrophobe surfactants that can be tailored for particular uses The following definitions of terms apply throughout the specification and claims.

For methods of treating a hydrocarbon-bearing formation and/or a well bore, the term "treating" includes placing a chemical (e.g., a fluorochemical, cationic polymer, or corrosion inhibitor) within a hydrocarbon-bearing formation using any suitable manner known in the art (e.g., pumping, injecting, pouring, releasing, displacing, spotting, or circulating the chemical into a well, well bore, or hydrocarbon-bearing formation).

The term "polymer" refers to a molecule having a structure that essentially includes the multiple repetitions of units derived, actually or conceptually, from molecules of low relative molecular mass. The term "polymer" includes "oligomer".

The term "bonded" refers to having at least one of covalent bonding, hydrogen bonding, ionic bonding, Van Der Waals interactions, pi interactions, London forces, or electrostatic interactions.

The term "productivity" as applied to a well refers to the capacity of a well to produce hydrocarbons; that is, the ratio of the hydrocarbon flow rate to the pressure drop, where the pressure drop is the difference between the average reservoir pressure and the flowing bottom hole well pressure (i.e., flow per unit of driving force). This term is not pertinent to enhanced oil recovery. It applies to near wellbore treatments such as the 3M treatment, but here the idea is to flood the entire reservoir with chemical solutions to mobilize and displace the oil to the production wells.

"Alkyl group" and the prefix "alk-" are inclusive of both straight chain and branched chain groups and of cyclic groups having up to 30 carbons (in some embodiments, up to 20, 15, 12, 10, 8, 7, 6, or 5 carbons) unless otherwise specified. Cyclic groups can be monocyclic or polycyclic and, in some embodiments, have from 3 to 10 ring carbon atoms.

"Alkylene" is the divalent form of the "alkyl" groups defined above.

"Arylalkylene" refers to an "alkylene" moiety to which an aryl group is attached.

The term "aryl" as used herein includes carbocyclic aromatic rings or ring systems, for example, having 1, 2, or 3 rings and optionally containing at least one heteroatom (e.g., O, S, or N) in the ring. Examples of aryl groups include phenyl, naphthyl, biphenyl, fluorenyl as well as furyl, thienyl, pyridyl, quinolinyl, isoquinolinyl, indolyl, isoindolyl, triazolyl, pyrrolyl, tetrazolyl, imidazolyl, pyrazolyl, oxazolyl, and thiazolyl.

"Arylene" is the divalent form of the "aryl" groups defined above.

Referring to FIG. 1, an exemplary offshore oil platform is schematically illustrated and generally designated 10. Semi-submersible platform 12 is centered over submerged hydrocarbon-bearing formation 14 located below sea floor 16. Subsea conduit 18 extends from deck 20 of platform 12 to wellhead installation 22 including blowout preventers 24. Platform 12 is shown with hoisting apparatus 26 and derrick 28 for raising and lowering pipe strings such as work string 30.

Wellbore 32 extends through the various earth strata including hydrocarbon-bearing formation 14. Casing 34 is cemented within wellbore 32 by cement 36. Work string 30 may include various tools including, for example, sand control screen assembly 38 which is positioned within wellbore 32 adjacent to hydrocarbon-bearing formation 14. Also extending from platform 12 through wellbore 32 is fluid delivery tube 40 having fluid or gas discharge section 42 positioned adjacent to hydrocarbon-bearing formation 14, shown with production zone 48 between packers 44, 46. When it is desired to treat the near-wellbore region of hydrocarbon-bearing formation 14 adjacent to production zone 48, work string 30 and fluid delivery tube 40 are lowered through casing 34 until sand control screen assembly 38 and fluid discharge section 42 are positioned adjacent to the near-wellbore region of hydrocarbon-bearing formation 14 including perforations 50. Thereafter, a composition described herein is pumped down delivery tube 40 to progressively treat the near-wellbore region of hydrocarbon-bearing formation 14.

Phase Behavior Procedures

Phase Behavior Screening. Phase behavior experiments have been used to characterize chemicals for EOR. There are many benefits in using phase behavior as a screening method. Phase Behavior studies are used to determine: (1) the effect of electrolytes; (2) oil solubilization, IFT reduction, (3) microemulsion densities; (4) surfactant and microemulsion viscosities; (5) coalescence times; (6) identify optimal surfactant-cosolvent formulations; and/or (7) identify optimal formulation for coreflood studies.

Thermodynamically stable phase can form with oil, water and surfactant mixtures. Surfactants form micellar structures at concentrations above the critical micelle concentration (CMC). The emulsion coalesces into a separate phase at the oil-water interface and is referred to as a microemulsion. A microemulsion is a surfactant-rich distinct phase consisting of surfactant, oil and water and possibly co-solvents and other components. This phase is thermodynamically stable in the sense that it will return to the same phase volume at a given temperature. Some workers in the past have added additional requirements, but for the purposes of this engineering study, the only requirement will be that the microemulsion is a thermodynamically stable phase.

The phase transition is examined by keeping all variables fixed except for the scanning variable. The scan variable is changed over a series of pipettes and may include, but is not limited to, salinity, temperature, chemical (surfactant, alcohol, electrolyte), oil, which is sometimes characterized by its equivalent alkane carbon number (EACN), and surfactant structure, which is sometimes characterized by its hydrophilic-lipophilic balance (HLB). The phase transition was first characterized by Winsor (1954) into three regions: Type I—excess oleic phase, Type III—aqueous, microemulsion and oleic phases, and the Type II—excess aqueous phase. The phase transition boundaries and some common terminology are described as follows: Type I to III—lower critical salinity, Type III to II—upper critical salinity, oil solubilization ratio ($V_o/V_s$), water solubilization ratio ($V_w/V_s$), the solubilization value where the oil and water solubilization ratios are equal is called the Optimum Solubilization Ratio ($\sigma^*$), and the electrolyte concentration where the optimum solubilization ratio occurs is referred to as the Optimal Salinity ($S^*$).

Determining Interfacial Tension. Efficient use of time and lab resources can lead to valuable results when conducting phase behavior scans. A correlation between oil and water solubilization ratios and interfacial tension was suggested by Healy and Reed (1976) and a theoretical relationship was later derived by Chun Huh (1979). Lowest oil-water IFT occurs at optimum solubilization as shown by the Chun Huh theory. This is equated to an interfacial tension through the Chun Huh equation, where IFT varies with the inverse square of the solubilization ratio:

$$\gamma = \frac{C}{\sigma^2} \tag{1}$$

For most crude oils and microemulsions, C=0.3 is a good approximation. Therefore, a quick and convenient way to estimate IFT is to measure phase behavior and use the Chun-Huh equation to calculate IFT. The IFT between microemulsions and water and/or oil can be very difficult and time consuming to measure and is subject to larger errors, so using the phase behavior approach to screen hundreds of combinations of surfactants, co-surfactants, co-solvents, electrolytes, oil, and so forth is not only simpler and faster, but avoids the measurement problems and errors associated with measuring IFT especially of combinations that show complex behavior (gels and so forth) and will be screened out anyway. Once a good formulation has been identified, then it is still a good idea to measure IFT.

Equipment. Phase behavior experiments are created with the following materials and equipment.

Mass Balance. Mass balances are used to measure chemicals for mixtures and determine initial saturation values of cores.

Water Deionizer. Deionized (DI) water is prepared for use with all the experimental solutions using a Nanopure™ filter system. This filter uses a recirculation pump and monitors the water resistivity to indicate when the ions have been removed. Water is passed through a 0.45 micron filter to eliminate undesired particles and microorganisms prior to use.

Borosilicate Pipettes. Standard 5 mL borosilicate pipettes with 0.1 mL markings are used to create phase behavior scans as well as run dilution experiments with aqueous solutions. Ends are sealed using a propane and oxygen flame.

Pipette Repeater. An Eppendorf Repeater Plus® instrument is used for most of the pipetting. This is a handheld dispenser calibrated to deliver between 25 microliter and 1 ml increments. Disposable tips are used to avoid contamination between stocks and allow for ease of operation and consistency.

Propane-oxygen Torch. A mixture of propane and oxygen gas is directed through a Bernz-O-Matic flame nozzle to create a hot flame about ½ inch long. This torch is used to flame-seal the glass pipettes used in phase behavior experiments.

Convection Ovens. Several convection ovens are used to incubate the phase behaviors and core flood experiments at the reservoir temperatures. The phase behavior pipettes are primarily kept in Blue M and Memmert ovens that are monitored with mercury thermometers and oven temperature gauges to ensure temperature fluctuations are kept at a minimal between recordings. A large custom built flow oven was used to house most of the core flood experiments and enabled fluid injection and collection to be done at reservoir temperature.

pH Meter. An ORION research model 701/digital ion analyzer with a pH electrode is used to measure the pH of most aqueous samples to obtain more accurate readings. This is calibrated with 4.0, 7.0 and 10.0 pH solutions. For rough measurements of pH, indicator papers are used with several drops of the sampled fluid.

Phase Behavior Calculations. The oil and water solubilization ratios are calculated from interface measurements taken from phase behavior pipettes. These interfaces are recorded over time as the mixtures approached equilibrium and the volume of any macroemulsions that initially formed decreased or disappeared. The procedure for creating phase behavior experiments will be discussed later.

Oil Solubilization Ratio. The oil solubilization ratio is defined as the volume of oil solubilized divided by the volume of surfactant in microemulsion. All the surfactant is presumed to be in the emulsion phase. The oil solubilization ratio is applied for Winsor type I and type III behavior. The volume of oil solubilized is found by reading the change between initial aqueous level and excess oil (top) interface level. The oil solubilization parameter is calculated as follows:

$$\sigma_o = \frac{V_o}{V_s} \tag{2}$$

$\sigma_o$=oil solubilization ratio
$V_o$=volume of oil solubilized
$V_s$=volume of surfactant Water Solubilization Ratio. The water solubilization ratio is defined as the volume of water solubilized divided by the volume of surfactant in microemulsion. All the surfactant is presumed to be in the emulsion phase. The water solubilization ratio is applied for Winsor type III and type II behavior. The volume of water solubilized is found by reading the change between initial aqueous level and excess water (bottom) interface level. The water solubilization parameter is calculated as follows:

$$\sigma_w = \frac{V_w}{V_s} \tag{3}$$

$\sigma_w$=water solubilization ratio
$V_w$=volume of water solubilized

Optimum Solubilization Ratio. The optimum solubilization ratio occurs where the oil and water solubilization is equal. The coarse nature of phase behavior screening often does not include a data point at optimum, so the solubilization curves are drawn for the oil and water solubilization and the intersection of these two curves is defined as the optimum. The following is true for the optimum solubilization ratio:

$$\sigma_o = \sigma_\omega = \sigma^* \tag{4}$$

$\sigma^*$=optimum solubilization parameter

Phase Behavior Methodology. The methods for creating, measuring and recording observations are described in this section. Scans are made using a variety of electrolyte mixtures described below. Oil is added to most aqueous surfactant solutions to see if a microemulsion formed, how long it took to form and equilibrate if it formed, what type of microemulsion formed and some of its properties such as viscosity. However, the behavior of aqueous mixtures without oil added is also important and is also done in some cases to determine if the aqueous solution is clear and stable over time, becomes cloudy or separated into more than one phase.

Preparation of samples. Phase behavior samples are made by first preparing surfactant stock solutions and combining them with brine stock solutions in order to observe the behavior of the mixtures over a range of salinities. All the experiments are created at or above 0.1 wt % active surfactant concentration, which is above the typical CMC of the surfactant.

Solution Preparation. Surfactant stocks are based on active weight-percent surfactant (and co-surfactant when incorporated). The masses of surfactant, co-surfactant, co-solvent and de-ionized water (DI) are measured out on a balance and mixed in glass jars using magnetic stir bars. The order of addition is recorded on a mixing sheet along with actual masses added and the pH of the final solution. Brine solutions are created at the necessary weight percent concentrations for making the scans.

Surfactant Stock. The chemicals being tested are first mixed in a concentrated stock solution that usually consisted of a primary surfactant, co-solvent and/or co-surfactant along with de-ionized water. The quantity of chemical added is calculated based on activity and measured by weight percent of total solution. Initial experiments are at about 1-3% active surfactant so that the volume of the middle microemulsion phase would be large enough for accurate measurements assuming a solubilization ratio of at least 10 at optimum salinity.

Polymer Stock. Often these stocks were quite viscous and made pipetting difficult so they are diluted with de-ionized water accordingly to improve ease of handling. Mixtures with polymer are made only for those surfactant formulations that showed good behavior and merited additional study for possible testing in core floods. Consequently, scans including polymer are limited since they are done only as a final evaluation of compatibility with the surfactant.

Pipetting Procedure. Phase behavior components are added volumetrically into 5 ml pipettes using an Eppendorf Repeater Plus or similar pipetting instrument. Surfactant and brine stocks are mixed with DI water into labeled pipettes and brought to temperature before agitation. Almost all of the phase behavior experiments are initially created with a water oil ratio (WOR) of 1:1, which involved mixing 2 ml of the aqueous phase with 2 ml of the evaluated crude oil or hydrocarbon, and different WOR experiments are mixed accordingly. The typical phase behavior scan consisted of 10-20 pipettes, each pipette being recognized as a data point in the series.

Order of Addition. Consideration had to be given to the addition of the components since the concentrations are often several fold greater than the final concentration. Therefore, an order is established to prevent any adverse effects resulting from surfactant or polymer coming into direct contact with the concentrated electrolytes. The desired sample compositions are made by combining the stocks in the following order: (1) Electrolyte stock(s); (2) De-ionized water; (3) Surfactant stock; (4) Polymer stock; and (5) Crude oil or hydrocarbon. Any air bubbles trapped in the bottom of the pipettes are tapped out (prior to the addition of surfactant to avoid bubbles from forming).

Initial Observations. Once the components are added to the pipettes, sufficient time is allotted to allow all the fluid to drain down the sides. Then aqueous fluid levels are recorded before the addition of oil. These measurements are marked on record sheets. Levels and interfaces are recorded on these documents with comments over several days and additional sheets are printed as necessary.

Sealing and Mixing. The pipettes are blanketed with argon gas to prevent the ignition of any volatile gas present by the flame sealing procedure. The tubes are then sealed with the propane-oxygen torch to prevent loss of additional volatiles when placed in the oven. Pipettes are arranged on the racks to coincide with the change in the scan variable. Once the phase behavior scan is given sufficient time to reach reservoir temperature (15-30 minutes), the pipettes are inverted several times provide adequate mixing. Tubes are observed for low tension upon mixing by looking at droplet size and how uniform the mixture appeared. Then the solutions are allowed to equilibrate over time and interface levels are recorded to determine equilibration time and surfactant performance.

Measurements and Observations. Phase behavior experiments are allowed to equilibrate in oven that is set to the reservoir temperature for the crude oil being tested. The fluid levels in the pipettes are recorded periodically and the trend in the phase behavior observed over time. Equilibrium behavior is assumed when fluid levels ceased to change within the margin of error for reading the samples.

Fluid Interfaces. The fluid interfaces are the most crucial element of phase behavior experiments. From them, the phase volumes are determined and the solubilization ratios are calculated. The top and bottom interfaces are recorded as the scan transitioned from an oil-in-water microemulsion to a water-in-oil microemulsion. Initial readings are taken one day after initial agitation and sometimes within hours of agitation if coalescence appeared to happen rapidly. Measurements are taken thereafter at increasing time intervals (for example, one day, four days, one week, two weeks, one month and so on) until equilibrium is reached or the experiment is deemed unessential or uninteresting for continued observation.

Comparative Examples. Surfactant formulation mimicking inexpensive Guerbet surfactant with C32-7PO-6EO sulfate/C16-187PO-6EO sulfate (85%/15%).

Figure 2A:
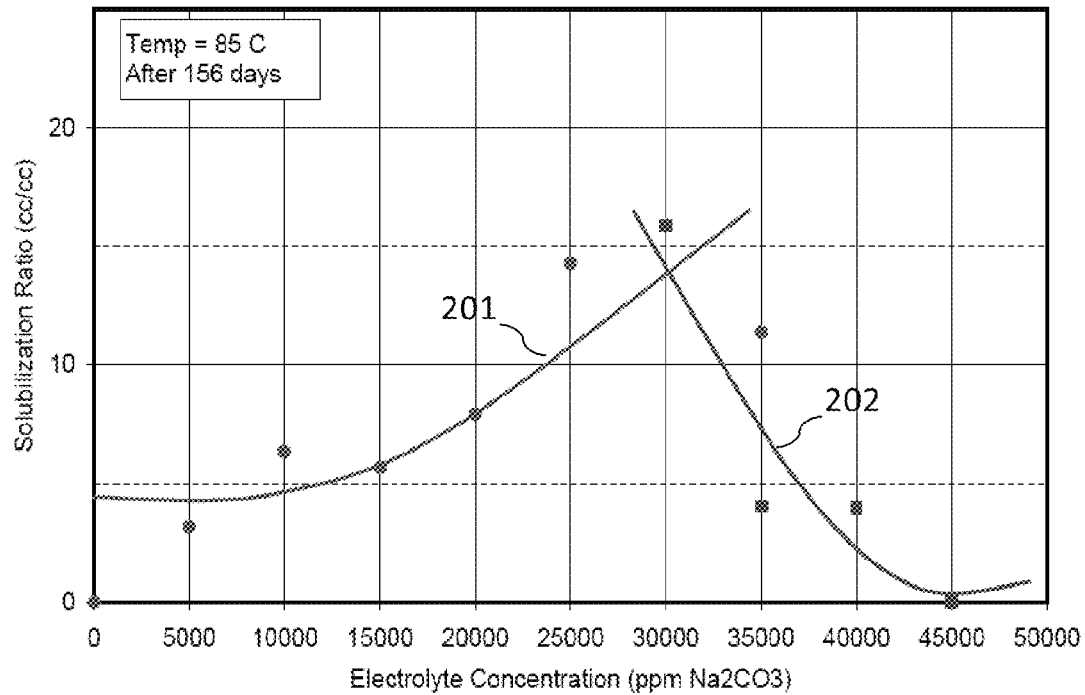
FIG. 2A is a phase behavior plot for a study with 50% crude oil comprising 0.3% $C_{32}$-7PO-6EO sulfate, 0.3% $C_{20-24}$ IOS (internal olefin sulfonate) at 85° C.
Figure 2B:
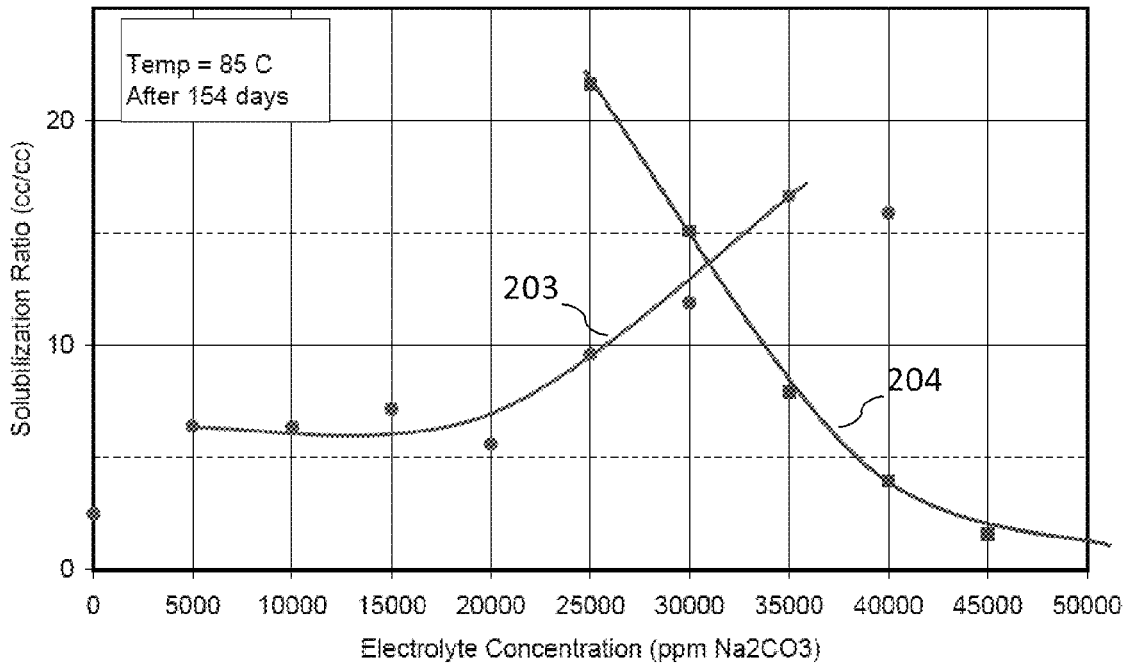
FIG. 2B is a phase behavior plot for a study with 50% crude oil comprising 0.3% $C_{32}$-7PO-6EO Sulfate (15% monomer $C_{16-18}$-7PO-6EO Sulfate), 0.3% $C_{20-24}$ IOS.

FIG. 2A is a phase behavior plot for a study with 50% crude oil comprising 0.3% $C_{32}$-7PO-6EO sulfate, 0.3% $C_{20-24}$ IOS at 85° C. (curve 201 being the oil solubilization ratios and curve 202 being the water solubilization ratios). FIG. 2B is a phase behavior plot for a study with 50% crude oil comprising 0.3% $C_{32}$-7PO-6EO Sulfate (15% monomer $C_{16-18}$-7PO-6EO Sulfate), 0.3% C20-24 IOS (curve 203 being the oil solubilization ratios and curve 204 being the water solubilization ratios)

Tables 1A and 1B (in FIGS. 3 and 4, respectively) shows phase behavior data recording sheets corresponding to plots shown in FIGS. 2A and 2B, respectively. Sample calculations for determining solubilization ratios and the interfacial tension are also shown.

At the optimum solubilization ratio (where oil and water solubilization are same) the interfacial tension (IFT) at oil-middle phase microemulsion and middle phase microemulsion-aqueous are the same. The IFT at optimum solubilization is widely determined by using Chun-Huh's relation (Eq. 1). For most crude oils C=0.3 is a good approximation. For both systems, shown in FIGS. 2A and 2B the IFT corresponding to optimum solubilization ratio of 13.5 cc/cc is: IFT, $\gamma=0.3/13.5^2=0.0016$ dynes/cm, which is regarded as ultralow. Thus, the inexpensive Guerbet derivative is as good as the pure Guerbet product.

Figure 4:
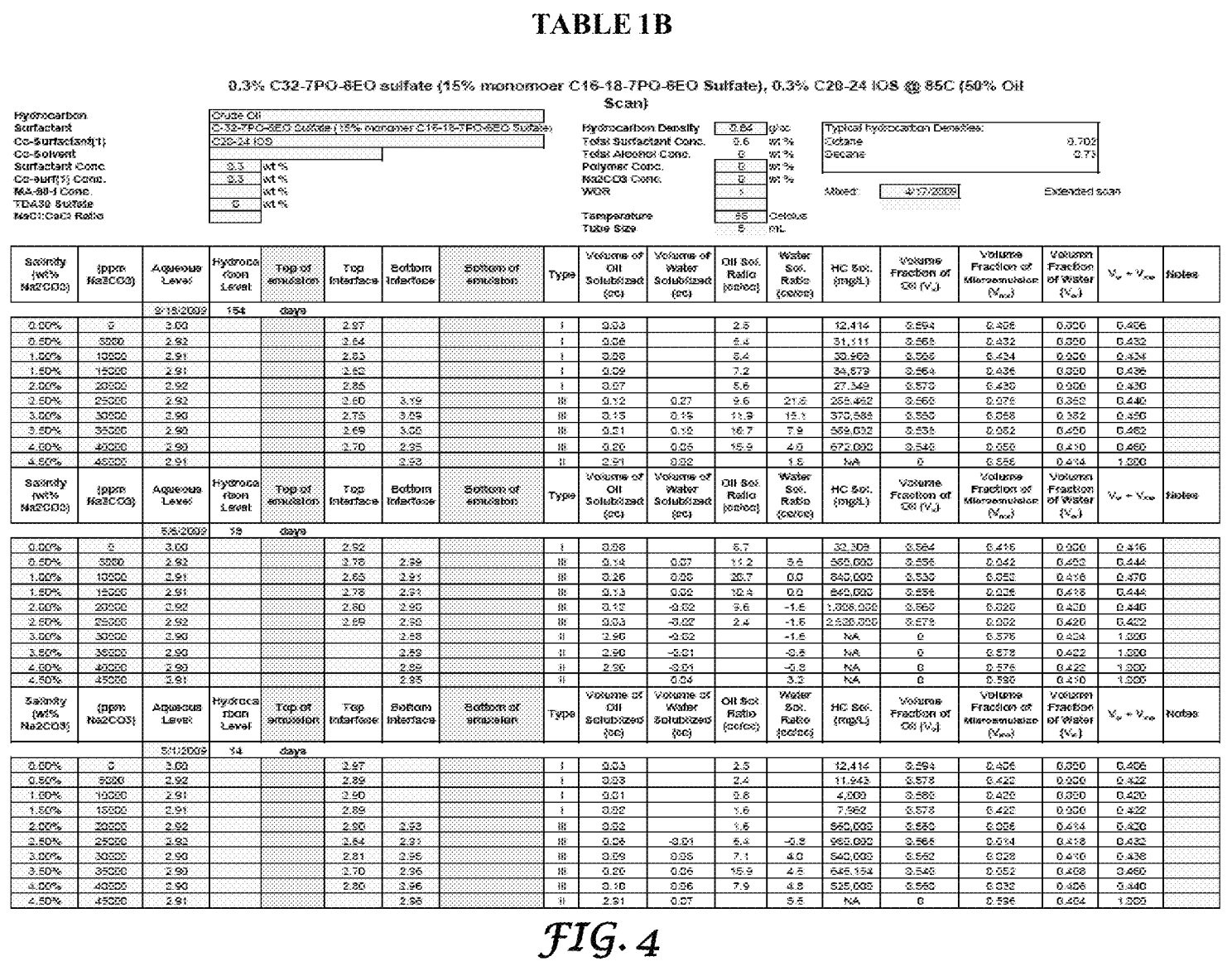

Table 1A: Phase behavior data recording sheet. (FIG. 3)
Table 1B: Phase behavior data recording sheet (FIG. 4).

Surfactant availability: C20-24-IOS is made from 20-24 carbon internal olefin via SO3 sulfonation followed by neutralization, which is available from Stepan Co. C32-7PO-6EO Sulfate was made from 32 carbon Guerbet alcohol via addition of 7 moles of PO, 6 moles of EO followed by $SO_3$ sulfonation and neutralization. C16-18-7-PO-6EO sulfate was made from 16-18-carbon alcohol and functionalized similarly. Both of these materials came from Harcros Chemicals, Inc.

The following examples and experiments, as well as, the other examples and experiments described herein, are presented to further illustrate the invention and, are not to be construed as unduly limiting the scope of this invention.

In the following examples and experiments, Guerbet alkoxylates, including C20-7PO-10EO—OH, C32-7PO-14EO—OH, were obtained from Harcros Chemicals, Inc. and were sulfated via standard sulfamic acid sulfation as being practiced commercially. The surfactant C16-18-7PO-5EO sulfate was also obtained from Harcros Chemicals, Inc. and were used as received.

The surfactants C16-17-7PO sulfate, C13-7PO sulfate, and C20-24 IOS (internal olefin sulfonate) were obtained from Stepan Company and were used as received.

The surfactants C12-15-3EO sulfate and C12-15-12EO sulfate were obtained from Shell Chemical Company and were used as received.

The salts used to make brine (for example sodium chloride, sodium carbonate, and sodium sulfate) was obtained from Fisher Chemical and used as received.

The co-solvent triethylene glycol mono butyl ether (TEGBE) was purchased from Aldrich Chemicals and used as received.

The polymer Flopaam 3630s was obtained from SNF.

Hydrolytic Stability of Alkoxy Sulfates

The hydrolytic stability of alkoxy sulfate surfactants at elevated temperatures were tested by studying surfactant solutions over time at temperatures of 85, 100, and 120 DC. For visual evidence of surfactant hydrolysis, the non-sulfated form of the surfactant must phase separate from the aqueous solution while the sulfated form of the surfactant is completely soluble (i.e., the nonionic surfactant form must be above the cloud point at the conditions of the experiment thereby forming an oily precipitation layer). A 4× concentrated surfactant stock solution included the alkoxy sulfate surfactant in de-ionized (DI) water (18 ohm) or brine at a slightly basic pH. The salts used to make the brine (for example sodium chloride, sodium carbonate, and sodium sulfate) were obtained from Fisher Chemical and used as received.

The quantity of surfactant was calculated based on the activity and measured by weight percent of total solution. The stock solution was used to make 10 mL samples with 1% surfactant and specific amounts of alkali in labeled 20 mL glass ampules (Wheaton). Components were added volumetrically into the ampules using an Eppendorf Repeater Plus or similar pipetting instrument with removable plastic tips. The samples were then blanketed with argon gas and sealed with a propane-oxygen torch to prevent fluid loss. The samples were then placed in racks in convection ovens at the elevated temperatures. Visual observations were taken over time until the oily precipitate indicates surfactant hydrolysis. The time it took for the oily precipitate to form was reported as the decomposition time. Additionally, the hydrolysis of the sulfate surfactants was confirmed by NMR (nuclear magnetic resonance) analysis. The surfactant sample was diluted with $D_2O$ (Acros) and placed in 8 inch long glass NMR tubes (Wilmad LabGlass, 5 mm thin wall for 400 mHz). A Varian 400 mHz Direct Drive NMR with SMS sample changer is used to measure the surfactant samples.

While low interfacial tensions and high oil recoveries are achievable using low-cost ether sulfate surfactants (Flaaten 2008; Levitt 2006), traditionally ether sulfates (ES) have been found to have poor hydrolytic stability at elevated temperatures (>65° C.) (Talley, 1988). Testing of the present invention reveals that ES have enhanced stability and controlled decomposition under specific conditions where hydrolysis was greatly reduced even at elevated temperatures. The hydrolysis reaction of ES surfactants occurs as follows:

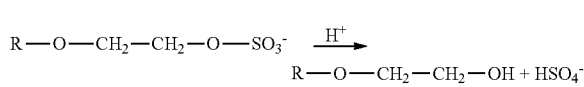

where R represents the rest of the surfactant head and tail structure. The hydrolysis of ES occurred rapidly under acidic conditions, which is the reason ES are commercially sold with a pH above 7 (usually about a pH of 8). Increasing the pH to about 10-11 greatly slowed hydrolysis of the ES even under elevated temperatures. As the hydrolysis reaction slowly occurred, $HSO_4^-$ was produced, which reduced the alkalinity (PH) and therefore increased the rate of hydrolysis. Therefore, a high starting pH is not the only factor that provides the hydrolytic stability to the ES surfactants. Under highly basic (very high pH) conditions, base catalyzed hydrolysis of the ES could occur and decompose the surfactant.

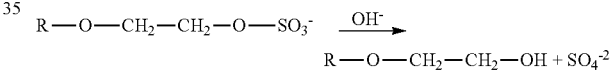

Therefore, a specific alkalinity (or pH) range was necessary to minimize the hydrolysis of ES surfactants at high temperatures. The temperature (T in Kelvin) dependence of the hydrolysis reaction rate follows the Arrhenius equation:

$$k = Ae^{\frac{-E_a}{RT}}$$

where k is the reaction rate coefficient, A is the pre-exponential factor, $E_a$ is the activation energy, and R is the ideal gas constant. As the temperature was elevated, the rate constant also increased and the hydrolysis reaction occurred more rapidly. For example, when the temperature was raised 10 K (or 10° C.) the rate of hydrolysis was approximately doubled and therefore the decomposition time was expected to be reduced by about half.

The decomposition time of $C_{16-17}$-7PO sulfate and $C_{12-15}$-3EO sulfate as a function of sodium carbonate concentration is presented in Table 2 for a temperature of 85° C.

TABLE 2

| Structure | $Na_2-CO_3$ Conc. (% wt) | Decomposition Time 85° C. | Theoretical Decomp. Time 85° C. |
|---|---|---|---|
| $C_{16-17}$-7PO Sulfate | 0.01-0.05% | <3 Months | |
| | 0.5-1% | >>13 Months (no oil) | 2.2 Years |

TABLE 2-continued

| Structure | $Na_2$—$CO_3$ Conc. (% wt) | Decomposition Time 85° C. | Theoretical Decomp. Time 85° C. |
|---|---|---|---|
| $C_{12-15}$-3EO Sulfate | 0.01-1% | >>13 Months (no oil) | 5.8 Years |
| $C_{12-15}$-12EO Sulfate | 0.05-0.50% | | 6.6 Years |
| $C_{16-18}$-7PO-5EO Sulfate | 0.1-0.25% | | 5.2 Years |
| | 0.5-2% | | 4.4 Years |
| $C_{20}$-7PO-10EO Sulfate | 0.05-0.25% | | 5.2 Years |
| | 0.5% | | 6.6 Years |
| | 1-2% | | 4.4 Years |

The addition of 0.01-1% of the alkali sodium carbonate to the aqueous solution of $C_{12-15}$-3EO sulfate minimized surfactant hydrolysis so that even after 13 months no decomposition of surfactant was observed. The decomposition (appearance of oil) of $C_{16-17}$-7PO sulfate occurred in less than 3 months for 0.01-0.05% sodium carbonate at 85° C., however at 0.5-1% sodium carbonate the surfactant was stable for 13 months with no signs of decomposition (no appearance of oil).

When the temperature was elevated to 100° C., the decomposition time was shorter than at 85° C. as seen in Table 3 as a function of sodium carbonate concentration.

TABLE 3

| Structure | $Na_2$—$CO_3$ Conc. (% wt) | Decomposition Time 100° C. | Theoretical Decomp. Time 100° C. |
|---|---|---|---|
| $C_{16-17}$-7PO Sulfate | 0.05% | <3 Months | |
| | 0.5-1% | 6.5-7 Months | 9 Months |
| $C_{12-15}$-3EO Sulfate | 0.01 | <0.1 Months | |
| | 0.05-0.5% | >13 Months (no oil) | 2.2 Years |
| | 1% | 12 Months | |
| $C_{12-15}$-12EO Sulfate | 0.05-0.50% | >13 Months (no oil) | 2.4 Years |
| | 1% | 12 Months | |
| $C_{16-18}$-7PO-5EO Sulfate | 0.1-0.25% | | 1.8 Years |
| | 0.5-2% | | 1.6 Years |
| $C_{20}$-7PO-10EO Sulfate | 0.05-0.25% | | 1.8 Years |
| | 0.5% | | 2.4 Years |
| | 1-2% | | 1.6 Years |

The decomposition time of $C_{16-17}$-7PO sulfate was 6.5-7 months (appearance of oil) with 0.5-1% sodium carbonate at 100° C. The higher temperature led to a higher rate of surfactant hydrolysis. The decomposition time of $C_{12-15}$-3EO sulfate and $C_{12-15}$-12EO sulfate were both greater than 13 months at 100° C. with 0.05-0.5% sodium carbonate. Decomposition had not occurred yet for these surfactants. The hydrolysis reaction was well controlled under these conditions within specific alkali ranges.

The decomposition time of the ES surfactants is presented in Table 4 at 126° C. as a function of the sodium carbonate concentration.

TABLE 4

| Structure | $Na_2$—$CO_3$ Conc. (% wt) | Decomposition Time 126° C. |
|---|---|---|
| $C_{16-17}$-7PO Sulfate | 1.5-2% | 1.5 Months |
| $C_{13}$-7PO Sulfate | 1-2% | 1.5 Months |
| $C_{12-15}$-3EO Sulfate | 0.05% | 4 Months |
| $C_{12-15}$-12EO Sulfate | 0.05-0.50% | 4.5 Months |
| $C_{16-18}$-7PO-5EO Sulfate | 0.05% | 0.3 Months |
| | 0.1-0.25% | 3.5 Months |
| | 0.5-2% | 3 Months |
| $C_{20}$-7PO-10EO Sulfate | 0.05-0.25% | 3-4 Months |
| | 0.5% | 4.5 Months |
| | 1-2% | 3 Months |

The hydrolysis of $C_{16-17}$-7PO sulfate occurred in 1.5 months at 126° C. with 1.5-2% sodium carbonate, which was about the decomposition time of about 1.3 months expected from the Arrhenius equation and 100° C. data. The importance of having the correct alkali concentration for minimizing ES hydrolysis can be seen in the decomposition time for $C_{20}$-7PO-10EO sulfate and $C_{16-18}$-7PO-5EO sulfate (Table 4) at 126° C. Hydrolysis of $C_{20}$-7PO-10EO sulfate occurred over 4.5 months with 0.5% sodium carbonate at 126° C. (Table 4). However, when only 0.05-0.25% sodium carbonate was added, the decomposition time of $C_{20}$-7PO-10EO sulfate was 3-4 months as the reduced concentration of alkali was neutralized faster.

On the other hand, increasing the amount of alkali to 1-2% sodium carbonate increased the rate of hydrolysis via base catalysis and the decomposition time decreased to 3 months. Similarly, hydrolysis of $C_{16-18}$-7PO-5EO sulfate was slowest over the sodium carbonate concentration range of 0.1-0.25% at 126° C. (Table 4) as the decomposition time decreased when the amount of alkali was either increased or decreased from this range.

The effect of the surfactant structure on decomposition time was determined by looking at three different classes of surfactants in Table 4: PO sulfates (the top two surfactants, $C_{16-17}$-7PO Sulfate and $C_{13}$-7PO Sulfate), PO-EO sulfates (the bottom two surfactants, $C_{16-18}$-7PO-5EO Sulfate and $C_{20}$-7PO-10EO Sulfate), and EO sulfates (the middle two surfactants, $C_{12-15}$-3EO Sulfate and $C_{12-15}$-12EO Sulfate). The PO sulfates were the least stable surfactants with decomposition times of only 1.5 months at 126° C. The decomposition time of the EO sulfate surfactants was almost 3× greater than that of the PO sulfates occurring over 4-4.5 months at 126° C.

The presence of EO units following the PO units in the structure, as in the PO-EO sulfate surfactants, increased the hydrolytic stability of surfactant beyond that of the PO sulfate surfactants. When 10 or more EO units were present after the PO units, the hydrolytic stability of the PO-EO surfactant was comparable to that of the EO sulfate surfactants (see $C_{20}$-7PO-10EO sulfate in Table 4). For example, $C_{16-18}$-7PO-5EO sulfate had a decomposition time of 3.5 months, which was much greater than the 1.5 months of the corresponding $C_{16-17}$-7PO sulfate surfactant (Table 4). Through the careful selection of ES surfactants and specific alkali concentrations, hydrolysis can be minimized and surfactants can remain stable for over 4.5 months at temperatures up to 126° C.

The decomposition time at 126° C. (Table 4) was used to estimate the theoretical decomposition time at 85 and 100° C. (Tables 2 and 3, respectively). At 85° C., the theoretical decomposition time for $C_{16-17}$-7PO sulfate was estimated at over 2 years (Table 2). For the more stable PO-EO and EO sulfate surfactants, the decomposition time was about 4-6 years at 85° C. (Table 2) and about 1.6-2.2 years at 100° C. (Table 3) with appropriate sodium carbonate concentrations.

Phase Behavior

The chemicals being tested were first mixed in a concentrated stock solution (typically 4×) that usually contained a primary surfactant, co-solvent and/or co-surfactant along with de-ionized water (18 ohm) or brine at a basic pH. The quantity of chemical added was calculated based on the activity of the chemicals and measured by weight percent of total solution (Flaaten 2008; Jackson 2006; Levitt 2006).

Standard 5 mL borosilicate pipettes with 0.1 mL markings were used to create phase behavior scans as well as run dilution experiments with aqueous solutions. Phase behavior components (including brine, alkali, DI water, and surfactant stock) were added volumetrically into the 5 ml pipettes using an Eppendorf Repeater Plus or similar pipetting instrument. Once the components were added to the pipettes, sufficient time was allotted to allow all the fluid to drain down the sides. Then aqueous fluid levels were recorded before the addition of the crude oil. The pipettes were blanketed with Argon gas to prevent the ignition of any volatile gas present by the flame sealing procedure. The tubes were then sealed with the propane-oxygen torch to prevent loss of additional volatiles when placed in the oven. Pipettes were arranged on the racks to coincide with the change in the scan variable (such as brine, alkali, or oil concentration).

Once the phase behavior scan was given sufficient time to reach reservoir temperature (15-60 minutes), the pipettes were inverted several times to provide adequate mixing. Tubes were observed for low tension upon mixing by looking at droplet size and how uniform the mixture appeared. Then the solutions were allowed to equilibrate over time and interface levels were recorded to determine equilibration time and surfactant performance.

Initial experiments used about 1-3% active surfactant so that the volume of the middle micro emulsion phase would be large enough for accurate measurements assuming a solubilization ratio of at least 10 at optimum salinity. Almost all of the phase behavior experiments were initially created with a water oil ratio (WOR) of 1:1, which involved mixing 2 ml of the aqueous phase with 2 ml of the evaluated crude oil or hydrocarbon, and different WOR experiments were mixed accordingly. The typical phase behavior scan consisted of 10-20 pipettes, each pipette being recognized as a data point in the series.

The oil and water solubilization ratios were calculated from interface measurements taken from the phase behavior pipettes. These interfaces were recorded over time as the mixtures approached equilibrium and the volume of any macroemulsions that initially formed decreased or disappeared. As discussed above, the oil solubilization ratio was defined as the volume of oil solubilized divided by the volume of surfactant in the microemulsion. All the surfactant was presumed to be in the emulsion phase. The volume of oil solubilized was found by reading the change between the initial aqueous level and the excess oil (top) interface level.

Similarly, and as discussed above, the water solubilization ratio was defined as the volume of water solubilized divided by the volume of surfactant in microemulsion (assumed to be the total surfactant volume). The volume of water solubilized was found by reading the change between the initial aqueous level and the excess water (bottom) interface level. The optimum solubilization ratio occurred where the oil and water solubilization was equal as determined by drawing oil and water solubilization ratio curves from the specific data points (one per pipette) (Levitt 2006).

Figure 5:
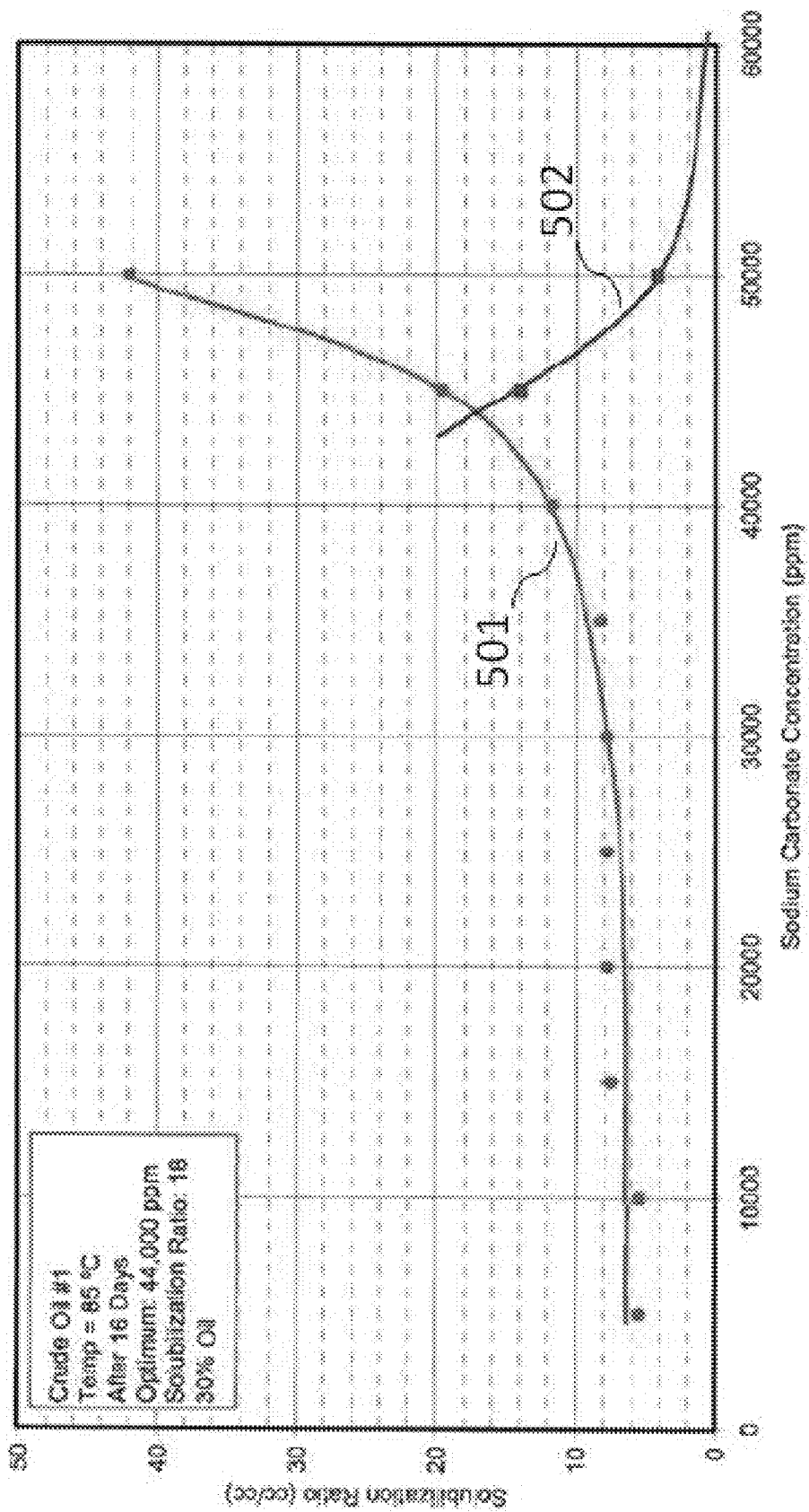
FIG. 5 is a phase behavior plot for a formulation of 0.25% $C_{32}$-7PO-14EO sulfate, 0.25% $C_{20-24}$ IOS, and 0.5% TEGBE (triethylene glycol mono butyl ether) at 85° C. (for 30% oil).

The solubilization ratio of 30% Crude Oil #1 (viscosity of 6.6 cP with high paraffin content, solid at room temperature) at 85° C. as a function of sodium carbonate concentration is presented in FIG. 5 for a formulation of 0.25% $C_{32}$-7PO-14EO sulfate, 0.25% $C_{20-24}$ IOS (internal olefin sulfonate), and 0.5% TEGBE (triethylene glycol mono butyl ether) (curve 501 being the oil solubility ratios and curve 502 being the water solubility ratio). As shown in FIG. 5, the optimum salinity of this formulation was 44,000 ppm with a solubilization ratio of 18 at this salinity. A solubilization ratio of 10 or higher corresponds to an interfacial tension of about 0.003 dyne/cm, which is sufficiently low to give high oil recovery for many chemical flooding applications.

Figure 6A:
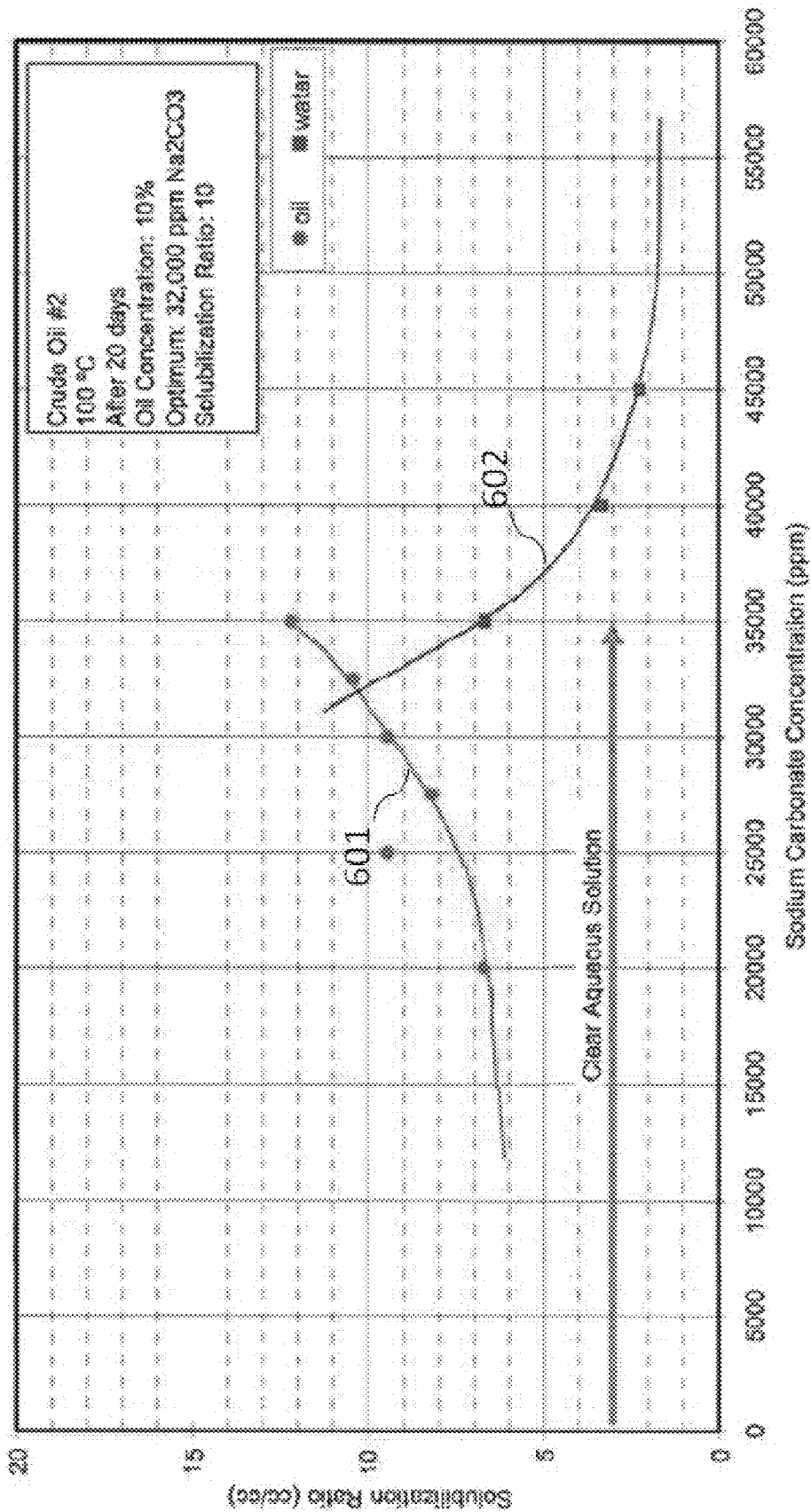
FIGS. 6A-6C are phase behavior plots for a formulation of 0.25% $C_{32}$-7PO-14EO sulfate, 0.25% $C_{20-24}$ IOS, and 0.5% TEGBE at 100° C. (for (A) 10%, (B) 30%, and (C) 50% oil, respectively).
Figure 6B:
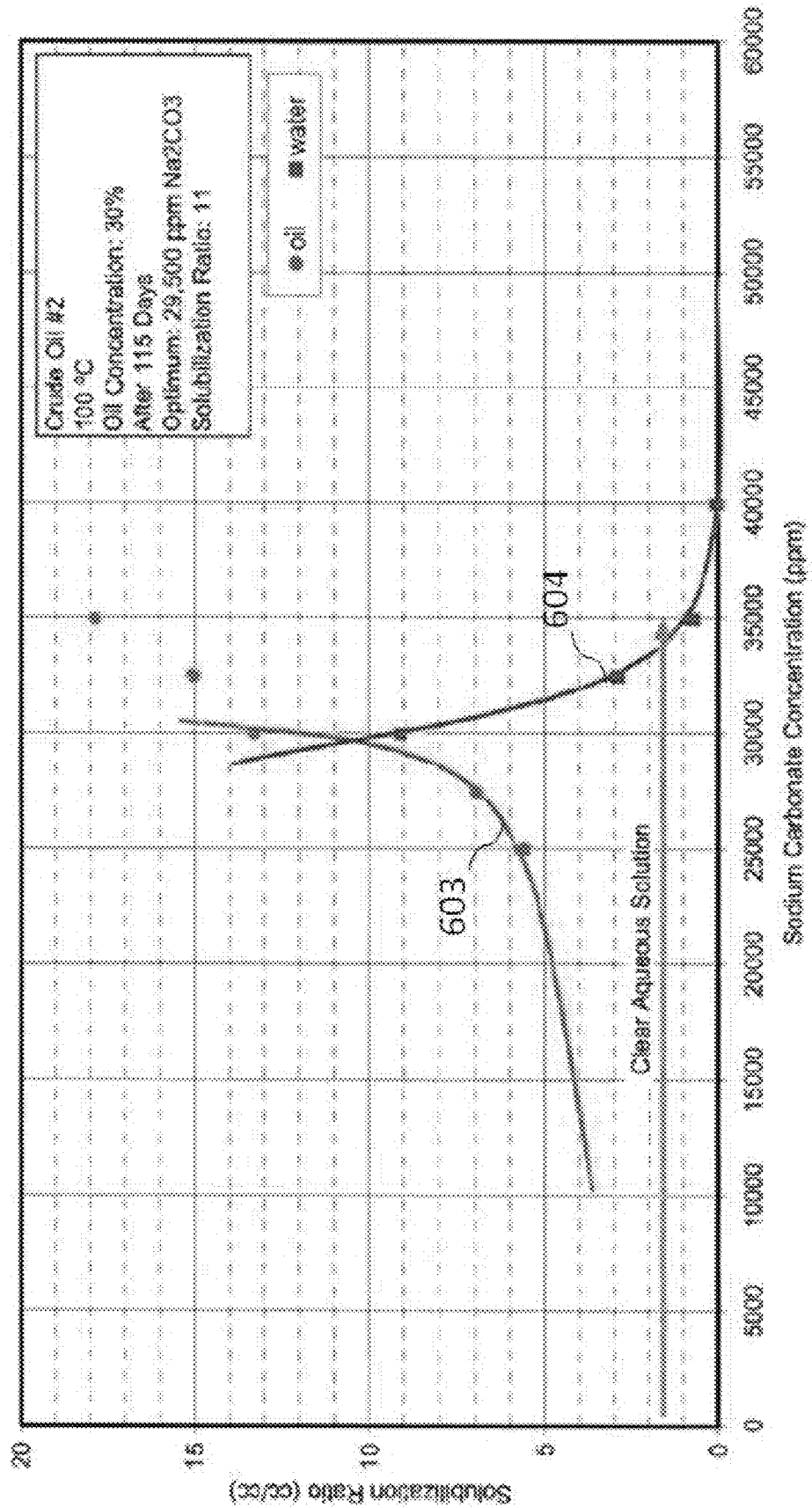
Figure 6C:
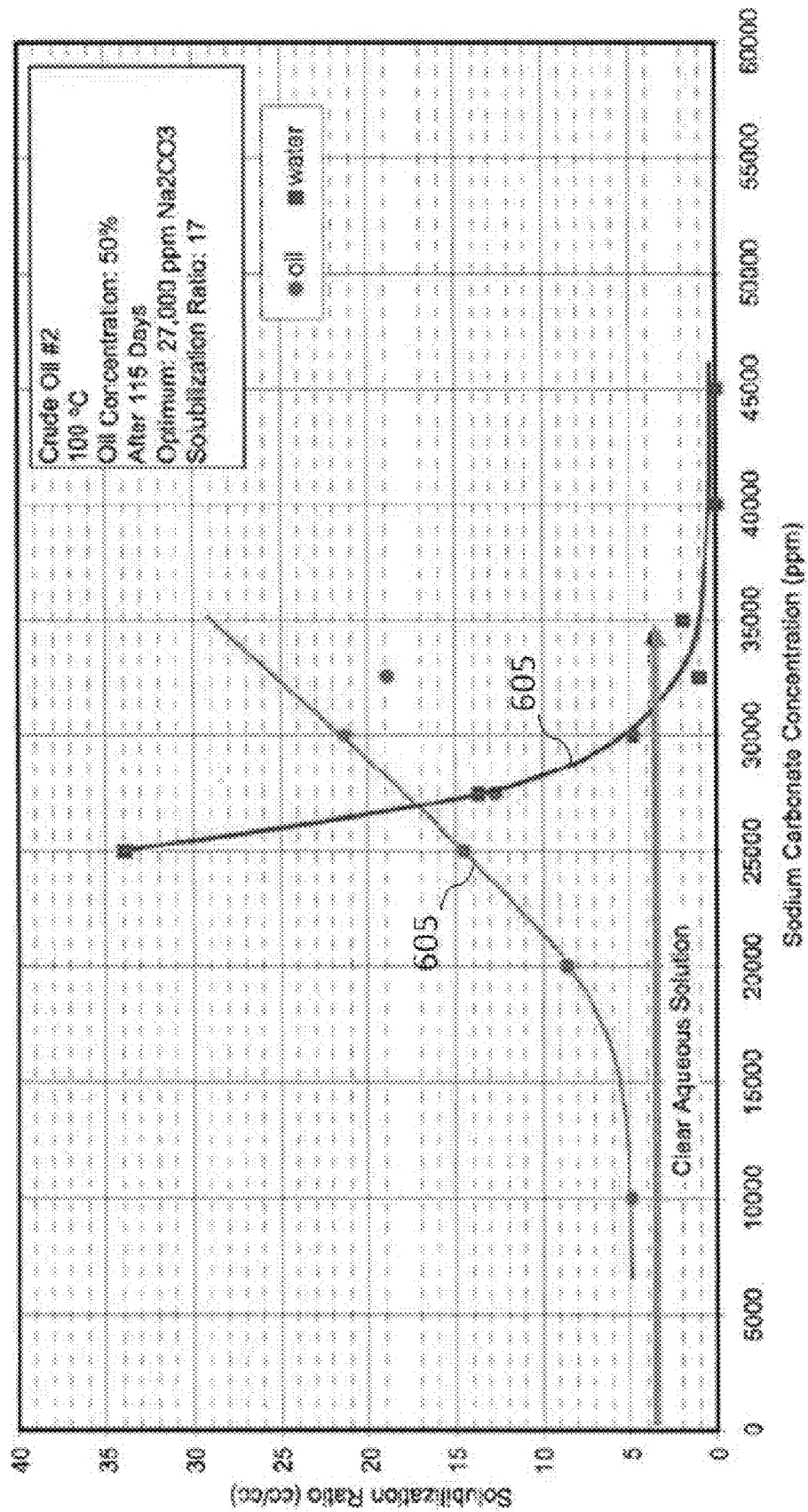

A formulation of 0.25% $C_{32}$-7PO-14EO sulfate, 0.25% $C_{20-24}$ IOS, and 0.5% TEGBE was also used with Crude Oil #2 (viscosity of 4.0 cP) at 100° C. The phase behavior of Crude Oil #2 with this surfactant formulation is presented in FIGS. 6A-6C for 10%, 30% and 50% oil, respectively. The optimum salinity changed from about 27,000-32,000 ppm sodium carbonate as the concentration of Crude Oil #2 was decreased. The solubilization ratio at the optimum salinity was 10 with 10% oil (FIG. 6A), 11 with 30% oil (FIG. 6B) and 17 with 50% oil (FIG. 6C). The aqueous solution of the surfactant formulation and 500 ppm Flopaam 3630s polymer was clear at 100° C. up to 35,000 ppm sodium carbonate, which indicated no phase separation of the aqueous solution. In addition to the ultra-low interfacial tensions, a low viscosity was observed for the middle phase microemulsions present in the three-phase region making this an attractive candidate for core flood experiments.

Core Flood

A core flood experiment was conducted using Bentheimer sandstone (properties in Table 5) at 100° C. (Flaaten 2008; Jackson 2006; Levitt 2006).

TABLE 5

| Core Property | Measurement |
| --- | --- |
| Mass | 1282 g |
| PV | 137.0 ml |
| Porosity | 0.217 |
| Length | 30.48 cm |
| Diameter | 5.13 cm |
| Length to Tap 1 | 7.5 cm |
| Length to Tap 2 | 15.0 cm |

TABLE 5-continued

| Core Property | Measurement |
| --- | --- |
| Length to Tap 3 | 22.5 cm |
| Cross Sectional Area | 20.68 cm$^2$ |
| Temperature | 100° C. |
| Air Permeability | ~2500 md |

Due to the high temperature (100° C.), a stainless steel core holder was used for the core flood. The core was subjected to a 500 psi confining pressure using a mineral oil pump. The Bentheimer sandstone had trace amounts of iron, thus 1000 ppm of sodium dithionite was used in the brine to keep the iron in the reduced state.

The core was initially saturated with Produce Brine (total dissolved solids at a concentration of 212.0 ppm (Ca$^{++}$ 27.0 ppm; Na$^+$ 53.3 ppm; SO$_4^{-2}$ 6.0 ppm; and Cl$^-$ 125.7 ppm)), and the pore volume of the core was determined by a high salinity tracer test. The core was then flooded with Crude Oil #2 (viscosity of 4.0 cP) at 100 psi pressure to saturate it with oil. Water flooding followed the oil flood to reach and measure the residual oil saturation. After the water flood, the ASP (alkali-surfactant-polymer) slug followed by the polymer drive was injected at 0.1 ml/min.

Oil saturations were calculated by material balance during each stage of the flood, and the permeability was calculated using the pressure drop across the core during flooding.

Differential pressure transducers were used to measure the pressure drop across several sections of the core during flooding.

The absolute pressure of the core was also measured. The pressure readings were recorded by computer during flooding.

Effluent from the core was captured in glass test tubes which were changed every 40 minutes for analysis.

Table 6 provides details the ASP slug and polymer drive (PD) composition and properties of the core flood experiment performed in the Bentheimer sandstone to evaluate the performance of the surfactant formulation starting at water flood residual oil saturation.

TABLE 6

| ASP Slug | Polymer Drive |
| --- | --- |
| Slug Size: 0.5 PV | Slug Size: 1.5 PV |
| 0.25% C$_{32}$-7PO-14EO sulfate | 900 ppm Flopaam 3630S |
| 0.25% C$_{20-24}$ IOS | 680 ppm of Na$_2$S$_2$O$_4$ (500 ppm S$_2$O$_4^{-2}$) |
| 0.5% TEGBE | 1000 ppm Na$_2$CO$_3$ |
| 2000 ppm Flopaam 3630S | Filtration Ratio: 1.01 |
| 30,000 ppm Na$_2$CO$_3$ | Frontal velocity: 1 ft/day |
| 680 ppm of Na$_2$S$_2$O$_4$ (500 ppm S$_2$O$_4^{-2}$) | Polymer Viscosity: 18 cp at 10 s$^{-1}$ and 100° C. |
| Filtration Ratio: 1.03 | |
| Frontal velocity: 1 ft/day | |
| ASP Slug Viscosity: 18 cp at 10 s$^{-1}$ and 100° C. | |

Figure 7:
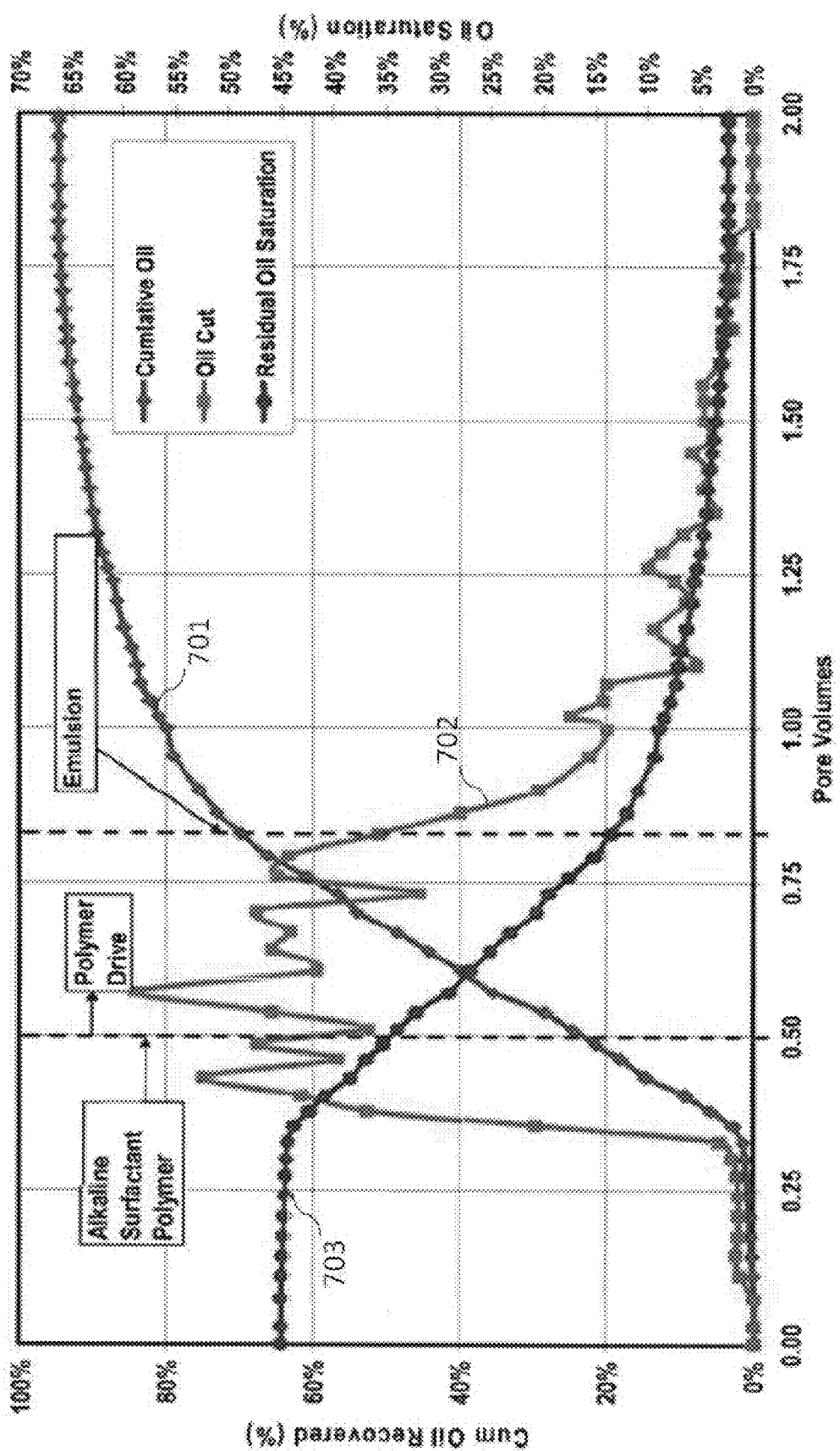
FIG. 7 is a plot of the cumulative oil recovered, the oil cut, and the oil saturation for a chemical core flood using formulation for FIGS. 6A-6C at 100° C. starting at waterflood residual oil saturation.

FIG. 7 is a plot of the cumulative oil recovered, the oil cut, and the oil saturation for this chemical core flood at 100° C. starting at waterflood residual oil saturation. Curve 701 is the cumulative oil recovered and is measured using the left axis of FIG. 7 (Cum Oil Recovered %). Curves 702 and 703 are, respectively, the oil cut and the oil saturation, and are measured using the right axis of FIG. 7 (Oil Saturation %).

Breakthrough of the oil bank occurred at about 0.35 PV. The average oil cut in the oil bank was about 65% (FIG. 7). The oil recovery was 94.7% of the residual oil saturation after water flood and the final oil saturation was about 0.02.

As shown above, The Guerbet reaction is a very attractive, commercially viable process for producing very large hydrophobe structures. Anionic surfactants are produced by the addition of Propylene oxide and/or ethylene oxide to the Guerbet alcohol, followed by sulfation. The hydrolysis of ether sulfate surfactants including these Guerbet alkoxy sulfates can be vastly reduced over a specific alkalinity range even at high temperatures. This allows for the enhanced stability or controlled decomposition of the ether sulfate surfactants at elevated temperatures. The decomposition time of ether sulfate surfactants is estimated to be about 1.6-2.2 years at 100° C. and 4-6 years at 85° C. Consequently, a wider selection of surfactant structures including the Guerbet alkoxy sulfates is available for use in high temperature reservoirs.

Microemulsion phase behavior and core flooding experiments at high temperatures carried out using the Guerbet alkoxy sulfates with appropriate co-surfactants show ultralow interfacial tension, low microemulsion viscosity, and high oil recovery for a wide variety of crude oils including some where no other really good formulation could be found. The present invention will both greatly increase the number of oil reservoirs where chemical EOR (surfactant-polymer, alkaline-surfactant-polymer and wettability alteration processes) is applicable and greatly improve its performance and robustness.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Pat. No. 4,011,273: Method for the production of Guerbet Alcohols utilizing insoluble lead catalysts.
U.S. Pat. No. 7,119,125: Bi-modal Guerbet alkoxy sulfate surfactants.
United States Patent Application No. 20080217064: Drilling fluid and methods.
Flaaten, A., et al., 2008, "A Systematic Laboratory Approach to Low-Cost, High-Performance Chemical Flooding," *SPE Improved Oil Recovery Symposium*, Tulsa, Okla. Apr. 19-23, 2008.
Jackson, A. C., 2006, "Experimental Study of the Benefits of Sodium Carbonate on Surfactants for EOR," University of Texas at Austin, Austin, 210.
Levitt, D. B., et al., 2006, "Identification and Evaluation of High-Performance EOR Surfactants," *SPE/DOE Symposium on Improved Oil Recovery*, Tulsa, Okla., Apr. 22-26, 2006.
Liu, Q., et al., 2007. "Surfactant enhanced alkaline flooding for western Canadian heavy oil recovery." *Colloids Surf, A FIELD Full Journal Title: Colloids and Surfaces, A: Physicochemical and Engineering Aspects,* 293(1-3): 63-71.
O'Lenick Jr., A. J., 2001, "Guerbet Chemistry," *Journal of Surfactants and Detergents,* 4(3): 311-315.
O'Lenick Jr., et al., 1996, "Effects of branching upon some surfactant properties of sulfated alcohols," *Journal of the American Oil Chemists Society,* 73(7): 935-937.
Talley, L. D., 1988, "Hydrolytic Stability of Alkylethoxy Sulfates," *SPE Reservoir Engineering,* 3(1): 235-242.

What is claimed is:

1. A method Comprising the steps of:
   (a) dimerizing a linear alcohol in the presence of a base to form a Guerbet alcohol, wherein yields a blend comprising between 85 wt % and 95 wt % of the Guerbet alcohol and between 5 wt % and 15 wt % of the unreacted linear alcohol;
   (b) converting the blend to a surfactant;
   (c) forming a surfactant formulation comprising the surfactant, an alkalinity generating agent, and a solvent, wherein the surfactant and the alkalinity generating agent are dissolved in the solvent.

2. The method of claim 1, wherein the step of converting the blend to a surfactant comprises an alkoxylation process.

3. The method of claim 2, wherein the surfactant has a chemical formula:

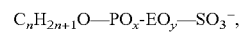

$$C_nH_{2n+1}O-PO_x\text{-}EO_y-SO_3^-,$$

wherein
   (i) PO is propylene oxide,
   (ii) EO is ethylene oxide,
   (iii) n is an integer between 12 and 44, inclusive,
   (iv) x is an integer between 0 and 50, inclusive,
   (v) y is an integer between 0 and 100, inclusive, and
   (vi) at least one of x and y is a non-zero integer.

4. The method of claim 3, wherein
   (A) the surfactant is an anionic ether sulfate surfactant,
   (B) the Guerbet alcohol formed in the step of dimerizing has a general formula of $C_nH_{2n+1}OH$,
   (C) during the step of converting, the Guerbet alcohol is alkoxylated to form an alkoxylated Guerbet alcohol, and
   (D) during the step of converting, the alkoxylated Guerbet alcohol is sulfated to produce the anionic ether sulfate surfactant.

5. The method of claim 4, wherein the anionic ether sulfate surfactant has a formula $C_3H_{65}O-PO_7\text{-}EO_6-SO_3^-$.

6. The method of claim 4, wherein n is 12, 15, 18, 20, 25, 28, 30, 35, 38, 40, 42, or 44.

7. The method of claim 4, wherein x is 0, 2, 5, 8, 10, 12, 14, 16, 18, 20, 30, 40, or 50.

8. The method of claim 4, wherein y is 0, 5, 10, 15, 20, 25, 30, 35, 40, 45, 50, 55, 60, 65, 70, 80, 90, or 100.

9. The method of claim 3, where x is a non-zero integer and y is a non-zero integer.

10. The method of claim 2, wherein the alkoxylation process adds an alkylene oxide to the Guerbet alcohol, wherein the alkylene oxide is selected from the group consisting of propylene oxide, ethylene oxide, and combinations thereof.

11. The method of claim 2, wherein the step of converting the alkoxylated blend to a surfactant comprises a sulfation process.

12. The method of claim 1, wherein the solvent is selected from the group consisting of water, polymer containing solutions, and combinations thereof.

13. The method of claim 12, wherein the solvent comprises water, and the water is hard brine or hard water.

14. The method of claim 1, wherein the base comprises NaOH, KOH, or both.

15. The method of claim 1, wherein the base is a catalyst for the step of dimerizing.

16. The method of claim 1, wherein the Guerbet alcohol is a branched alcohol hydrophobe.

17. The method of claim 1, wherein the linear alcohol has a general formula $C_nH_{2n+1}OH$, wherein n is an integer between 6 and 22, inclusive.

18. The method of claim 1, wherein the linear alcohol has a formula $C_{16}H_{33}OH$.

19. The method of claim 1, wherein the Guerbet alcohol is branched at about the mid-point of the carbon chain.

20. The method of claim 1, wherein the dimerization is carried out a temperature range of about 175° C. to about 275° C.

21. The method of claim 1, wherein the dimerization is carried out at a temperature selected from the group consisting of 175° C., 190° C., 200° C., 220° C., 230° C., 240° C., 250° C. and 275° C.

22. The method of claim 1, wherein the dimerization is carried out at 230° C.

23. The method of claim 1, wherein the step of converting the blend to a surfactant comprises a sulfation process.

24. The method of claim 1, wherein the surfactant is an anionic surfactant.

25. The method of claim 1, wherein the surfactant formulation comprises the alkalinity generating agent in an amount such that the surfactant is stable at 126° C.

26. The method of claim 1, wherein the surfactant formulation comprises between 0.01 wt % and 5 wt % of the alkalinity generating agent.

27. The method of claim 1, wherein the surfactant formulation comprises at least 0.1 wt % of the alkalinity generating agent.

28. The method of claim 1, wherein the surfactant formulation comprises between 0.5 wt % and 1 wt % of the alkalinity generating agent.

29. The method of claim 1, wherein the alkalinity generating agent is selected from the group consisting of alkali, earth metal hydroxides, NaOH, KOH, LiOH, ammonia, $Na_2CO_3$, $NaHCO_3$, Na-metaborate, sodium silicate, sodium orthosilicate, $EDTANa_4$, other polycarboxylates, and combinations thereof.

30. A composition comprising:
 (i) an anionic ether sulfate surfactant having a formula of:

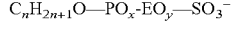

wherein
 (a) PO is propylene oxide,
 (b) EO is ethylene oxide,
 (c) n is an integer between 12 and 44, inclusive,
 (d) x is an integer between 0 and 50, inclusive, and
 (e) y is an integer between 0 and 100, inclusive;
 (ii) an alkalinity generating agent; and
 (iii) a solvent, wherein the anionic ether sulfate surfactant and the alkalinity generating agent are dissolved in the solvent.

31. The composition of claim 30, wherein the solvent is selected from the group consisting of water, polymer containing solutions, and combinations thereof.

32. The composition of claim 31, wherein the solvent comprises water, and the water is hard brine or hard water.

33. The composition of claim 30, wherein the anionic ether sulfate surfactant is produced by the process of
 (i) dimerizing a linear alcohol in the presence of a base to form a Guerbet alcohol, wherein yields a blend comprising between 85 wt % and 95 wt % of the Guerbet alcohol and between 5 wt % and 15 wt % of the unreacted linear alcohol,
 (ii) performing an alkoxylation process to add an alkylene oxide to the Guerbet alcohol, wherein the alkylene oxide is selected from the group consisting of propylene oxide, ethylene oxide, and combinations thereof,
 (iii) performing a sulfation process to the alkoxylated Guerbet alcohol to form the anionic ether sulfate surfactant.

34. The composition of claim 30, Wherein the composition is operable for use in an enhanced oil recovery (EOR) application.

35. The composition of claim 30, wherein the composition is opera r use in an environmental ground water cleanup application.

36. The composition of claim 30, wherein the anionic ether sulfate surfactant comprises $C_{32}H_{65}O$—$PO_7$-$EO_6$—$SO_3^-$ and $C_{16\text{-}18}$—$H_{33\text{-}37}$—O—$PO_7$-$EO_6$—$SO_3^-$.

37. The composition of claim 30, wherein the anionic ether sulfate surfactant comprises 85 wt % of $C_{32}H_{65}O$—$PO_7$-$EO_6$—$SO_3^-$ and 15 wt $C_{16\text{-}18}$—$H_{33\text{-}37}$—O—$PO_7$-$EO_6$—$SO_3^-$.

38. The composition of claim 30, wherein n is 12, 15, 18, 20, 22, 25, 28, 30, 35, 38, 40, 42, or 44.

39. The composition of claim 30, wherein x is 0, 2, 5, 8, 10, 12, 14, 16, 18, 20, 30, 40, or 50.

40. The composition of claim 30, wherein y is 0, 5, 10, 15, 20, 25, 30, 35, 40, 45, 50, 55, 60, 65, 70, 80, 90, or 100.

41. The composition of claim 30, wherein at least one of x and y is a non-zero integer.

42. The composition of claim 30, where x is a non-zero integer and y is a non-zero integer.

43. The composition of claim 30 further comprising an additional anionic surfactant selected from the group consisting of sulfate, sulfonate, carboxylate anion based surfactants, ether sulfates, ethoxy sulfates, propoxy sulfates, $C_{32}H_{65}O$—$PO_7$-$EO_6$—$SO_3^-$, $C_{12\text{-}15}$-3EO sulfates, $C_{12\text{-}15}$-12EO sulfates, $C_{16\text{-}17}$-7PO sulfates, $C_{13}$-7PO sulfates, $C_{16\text{-}18}$-7PO-5EO sulfates, $C_{20}$-7PO-10EO sulfate's, perfluorooctanoate (PFOA or PFO), perfluorooctanesulfonate (PFOS), sodium dodecyl sulfate (SDS), ammonium lauryl sulfate, alkyl sulfate salts, sodium lauryl ether sulfate (SLES), alkyl benzene sulfonate, soaps, fatty acid salts, and combinations thereof.

44. The composition of claim 30, wherein the alkalinity generating agent is selected from the group consisting of alkali earth metal hydroxides, NaOH, KOH, LiOH, ammonia, $Na_2CO_3$, $NaHCO_3$, Na-metaborate, sodium silicate, sodium orthosilicate, $EDTANa_4$, polycarboxylates, and combinations thereof.

45. The composition of claim 30, wherein the composition comprises between 0.01 wt % and 5 wt % of the alkalinity generating agent.

46. A method of using an anionic ether sulfate surfactant formulation for enhanced oil recovery from a hydrocarbon bearing formation comprising the steps of:
 (a) injecting an anionic ether sulfate surfactant composition into the hydrocarbon hearing formation at a temperature between 25° C. to 120° C., wherein,
 (i) the anionic ether sulfate composition comprises an anionic ether sulfate having a chemical formula

wherein (A) PO is propylene oxide, (B) EO is ethylene oxide, (C) n is an integer between 12 and 44, inclusive, (D) x is an integer between 0 and 50, inclusive, and (E) y is an integer between 0 and 100, inclusive, and
 (ii) the anionic ether sulfate composition is injected either alone or as an alkaline-surfactant-polymer formulation (ASP); and
 (b) injecting a polymer push solution to recover oil.

47. The method of claim 46, wherein the anionic ether sulfate surfactant composition further comprises water and an alkalinity generating agent.

48. The method of claim 47, wherein the water is either hard water or hard brine.

49. The method of claim 47, wherein the anionic ether sulfate surfactant composition comprises at least 0.1 wt % of the alkalinity generating agent.

50. The method of claim 47, wherein the anionic ether sulfate surfactant composition further comprises an additional anionic surfactant selected from the group consisting of sulfate, sultanate, carboxylate anion based surfactants, ether sulfates, ethoxy sulfates, propoxy sulfates, $C_{32}H_{65}O-PO_7-EO_6-SO_3^-$, $C_{12-15}$-3EO sulfates, $C_{12-15}$-12EO sulfates, $C_{16-17}$-7PO sulfates, $C_{13}$-7PO sulfates, $C_{16-18}$-7PO-5EO sulfates, $C_{20}$-7PO-10EO sulfates, perfluorooctanoate (PFOA or PFO), perfluorooctanesulfonate (PFOS), sodium dodecyl sulfate (SDS), ammonium lauryl sulfate, alkyl sulfate salts, sodium lauryl ether sulfate (SLES), alkyl benzene sulfonate, soaps, fatty acid salts, and combinations thereof.

51. The method of claim 47, wherein the alkalinity generating agent is selected from the group consisting of alkali earth metal hydroxides, NaOH, KOH, LiOH, ammonia, $Na_2CO_3$, $NaHCO_3$, Na-metaborate, sodium silicate, sodium orthosilicate, EDTANa$_4$, other polycarboxylates, and combinations thereof.

* * * * *

(12) EX PARTE REEXAMINATION CERTIFICATE (10780th)
United States Patent
Weerasooriya et al.

(10) Number: US 8,211,837 C1
(45) Certificate Issued: Dec. 22, 2015

(54) METHOD OF MANUFACTURE AND USE OF LARGE HYDROPHOBE ETHER SULFATE SURFACTANTS IN ENHANCED OIL RECOVERY (EOR) APPLICATIONS

(75) Inventors: Upali P. Weerasooriya, Austin, TX (US); Gary A. Pope, Cedar Park, TX (US); Quoc P. Nguyen, Austin, TX (US)

(73) Assignee: BOARD OF REGENTS, THE UNIVERSITY OF TEXAS SYSTEM, Austin, TX (US)

Reexamination Request:
No. 90/013,313, Aug. 5, 2014

Reexamination Certificate for:
Patent No.: 8,211,837
Issued: Jul. 3, 2012
Appl. No.: 12/887,858
Filed: Sep. 22, 2010

Related U.S. Application Data

(60) Provisional application No. 61/244,795, filed on Sep. 22, 2009.

(51) Int. Cl.
*C09K 8/584* (2006.01)
*C07C 305/00* (2006.01)
*C07D 303/34* (2006.01)
*C07D 301/00* (2006.01)

(52) U.S. Cl.
CPC .............. *C09K 8/584* (2013.01); *C07D 301/00* (2013.01); *C07D 303/34* (2013.01)

(58) Field of Classification Search
None
See application file for complete search history.

(56) References Cited

To view the complete listing of prior art documents cited during the proceeding for Reexamination Control Number 90/013,313, please refer to the USPTO's public Patent Application Information Retrieval (PAIR) system under the Display References tab.

*Primary Examiner* — Jerry D Johnson

(57) ABSTRACT

The present invention describes the method of making anionic ether sulfate surfactants by alkoxylation of a GA using PO and/or EO followed by a sulfation reaction. The GA of the present invention is made by a facile and inexpensive method that involves high temperature base catalyzed dimerization of a linear alcohol. The ether sulfate surfactants of the present invention find uses in EOR applications where it is used for solubilization and mobilization of oil and for environmental cleanup.

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 4, 10, 11, 14-16, 18, 22-24, 27 and 28 are cancelled.

Claims 1-3, 5-8, 21, 25, 26, 29, 30, 34-40, 43, 45-47 and 49 are determined to be patentable as amended.

Claims 9, 12, 13, 17, 19, 20, 31-33, 41, 42, 44, 48, 50 and 51, dependent on an amended claim, are determined to be patentable.

New claims 52-69 are added and determined to be patentable.

1. A method [Comprising] *comprising* the steps of:
   (a) dimerizing a linear alcohol in the presence of a base to form a Guerbet alcohol, wherein *the dimerization yields a blend comprising between 85 wt% and 95 wt% of the Guerbet alcohol and between 5 wt% and 15 wt% of the unreacted linear alcohol*;
   (b) converting the blend to [a] *an anionic ether sulfate* surfactant; *and*
   (c) *forming a surfactant formulation comprising the anionic ether sulfate surfactant, from 1 wt % to 5 wt % of an alkalinity generating agent, and a solvent, wherein the surfactant and the alkalinity generating agent are dissolved in the solvent, and wherein forming the surfactant formulation comprises adding an effective amount of the alkalinity generating agent to stabilize the anionic ether sulfate surfactant for at least three months at 85° C.*

2. The method of claim 1, wherein the step of converting the blend to [a] *the anionic ether sulfate* surfactant comprises an alkoxylation process *and a sulfation process*.

3. The method of claim 2, wherein the *anionic ether sulfate* surfactant has a chemical formula:

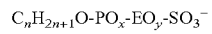

wherein
   (i) PO is propylene oxide,
   (ii) EO is ethylene oxide,
   (iii) $C_nH_{2n+1}O$ comprises a moiety derived from a Guerbet alcohol, where n is an integer between 12 and 44, inclusive,
   (iv) x is an integer between 0 and 50, inclusive,
   (v) y is an integer between 0 and 100, inclusive, and
   (vi) at least one of x and y is a non-zero integer.

5. The method of claim [4] *3*, wherein the anionic ether sulfate surfactant has a formula [$C_3H_{65}O-PO_7-EO_6-SO_3^-$] $C_{32}H_{65}O-PO_7-EO_6-SO_3^-$.

6. The method of claim [4] *3*, wherein n is [12, 15, 18, 20, 22, 25, 28, 30, 35, 38, 40, 42, or 44] *from 18 to 38*.

7. The method of claim [4] *3*, wherein x is [0, 2, 5, 8, 10, 12, 14, 16, 18, 20, 30, 40, or 50] *from greater than 20 to 50*.

8. The method of claim [4] *3*, wherein y is [0, 5, 10, 15, 20, 25, 30, 35, 40, 45, 50, 55, 60, 65, 70, 80, 90, or 100] *from greater than 20 to 100*.

21. The method of claim 1, wherein the dimerization is carried out at a temperature [selected from the group consisting of 175° C., 190° C., 200° C., 220° C., 230° C., 240° C., 250° C., and 275° C.] *of from about 230° C. to about 275° C.*.

25. The method of claim 1, wherein the surfactant formulation comprises the alkalinity generating agent in an amount such that the *anionic ether sulfate* surfactant is stable at 126° C.

26. The method of claim 1, wherein the surfactant formulation comprises [between 0.01] *from 1* wt % [and 5] *to 2* wt % of the alkalinity generating agent.

29. The method of claim 1, wherein the alkalinity generating agent is selected from the group consisting of alkali[,] earth metal hydroxides, NaOH, KOH, LiOH, ammonia, $Na_2CO_3$, $NaHCO_3$, Na-metaborate, sodium silicate, sodium orthosilicate, $EDTANa_4$, other polycarboxylates, and combinations thereof.

30. A composition comprising:
   (i) an anionic ether sulfate surfactant having a formula of:

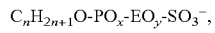

wherein
   (a) PO is propylene oxide,
   (b) EO is ethylene oxide,
   (c) $C_nH_{2n+1}O$ comprises a moiety derived from a Guerbet alcohol, where n is an integer between 12 and 44, inclusive,
   (d) x is an integer between 0 and 50, inclusive, and
   (e) y is an integer between 0 and 100, inclusive;
   (ii) *from 1 wt % to 5 wt % of* an alkalinity generating agent; and
   (iii) a solvent, wherein the anionic ether sulfate surfactant and the alkalinity generating agent are dissolved in the solvent, *and wherein alkalinity generating agent is present in the composition in an amount such that the anionic ether sulfate surfactant is stable for at least three months at 85° C.*

34. The composition of claim 30, [Wherein] *wherein* the composition is operable for use in an enhanced oil recovery (EOR) application.

35. The composition of claim 30, wherein the composition is [opera r] *operable* for use in an environmental groundwater cleanup application.

36. The composition of claim 30, wherein the anionic ether sulfate surfactant comprises $C_{32}H_{65}O-PO_7-EO_6-SO_3^-$ [and $C_{16-18}-H_{33-37}-O-PO_7-EO_6-SO_3^-$].

37. The composition of claim 30, wherein the anionic ether sulfate surfactant comprises [85 wt % of $C_{32}H_{65}O-PO_7-EO_6-SO_3^-$ and 15 wt] $C_{16-18}-H_{33-37}-O-PO_7-EO_6-SO_3^-$.

38. The composition of claim 30, wherein n is [12, 15, 18, 20, 22, 25, 28, 30, 35, 38, 40, 42, or 44] *from 18 to 38*.

39. The composition of claim 30, wherein x is [0, 2, 5, 8, 10, 12, 14, 16, 18, 20, 30, 40, or 50] *from greater than 20 to 50*.

40. The composition of claim 30, wherein y is [0, 5, 10, 15, 20, 25, 30, 35, 40, 45, 50, 55, 60, 65, 70, 80, 90, or 100] *from greater than 20 to 100*.

43. The composition of claim 30 further comprising an additional anionic surfactant selected from the group consisting of sulfate, sulfonate, carboxylate anion based surfactants, ether sulfates, ethoxy sulfates, propoxy sulfates, $C_{32}H_{65}O-PO_7-EO_6-SO_3^-$, $C_{12-15}$-3EO sulfates, $C_{12-15}$-12EO sulfates, $C_{16-17}$-7PO sulfates, $C_{13}$-7PO sulfates, $C_{16-18}$-7PO-5EO sulfates, $C_{20}$-7PO-10EO [sulfate's] *sulfates*, perfluorooctanoate (PFOA or PFO), perfluorooctanesulfonate (PFOS), sodium dodecyl sulfate (SDS), ammonium lauryl sulfate, alkyl sulfate salts, sodium lauryl ether sulfate (SLES), alkyl benzene sulfonate, soaps, fatty acid salts, and combinations thereof.

45. The composition of claim 30, wherein the composition comprises [between 0.01] *from 1* wt % [and 5] *to 2* wt % of the alkalinity generating agent.

46. A method of using an anionic ether sulfate surfactant [formulation] *composition* for enhanced oil recovery from a hydrocarbon bearing formation comprising the steps of:
 (a) injecting an anionic ether sulfate surfactant composition into the hydrocarbon [hearing] *bearing* formation at a temperature [between 25° C.] *of from 65° C.* to 120° C., wherein,
  (i) the anionic ether sulfate composition comprises *water, an alkalinity generating agent, and* an anionic ether sulfate having a chemical formula

wherein (A) PO is propylene oxide, (B) EO is ethylene oxide, (C) $C_nH_{2n+1}O$ comprises a moiety derived from a Guerbet alcohol, where n is an integer between 12 and 44, inclusive, (D) x is an integer between 0 and 50, inclusive, and (E) y is an integer between 0 and 100, inclusive, [and]
  (ii) *the alkalinity generating agent is present in the composition in an amount such that the anionic ether sulfate surfactant is stable for at least three months at 85° C., and*
  (iii) *the anionic ether sulfate composition is injected either alone or as an alkaline-surfactant-polymer formulation (ASP); and*
 (b) injecting a polymer push solution to recover oil.

47. The method of claim 46, wherein [the anionic ether sulfate surfactant composition further comprises water and an alkalinity generating agent] *the anionic ether sulfate surfactant composition comprises from 1 wt % to 5 wt % of the alkalinity generating agent.*

49. The method of claim 47, wherein the anionic ether sulfate surfactant composition comprises [at least 0.1 wt %] *from 1 wt % to 2 wt %* of the alkalinity generating agent.

52. *The method of claim 1, wherein the surfactant formulation has a pH of from about 10 to about 11.*

53. *The method of claim 6, wherein n is from 25 to 38.*

54. *The method of claim 3, wherein x is from greater than 20 to 50 and y is from greater than 20 to 100.*

55. *The composition of claim 30, wherein the composition comprises the alkalinity generating agent in an amount such that the anionic ether sulfate surfactant is stable at 126° C.*

56. *The composition of claim 30, wherein the composition has a pH of from about 10 to about 11.*

57. *The composition of claim 38, wherein n is from 25 to 38.*

58. *The composition of claim 30, wherein x is from greater than 20 to 50 and y is from greater than 20 to 100.*

59. *The method of claim 46, wherein step a comprises injecting the anionic ether sulfate surfactant composition into the hydrocarbon bearing formation at a temperature of from 85° C. to 120° C.*

60. *The method of claim 59, wherein step a comprises injecting the anionic ether sulfate surfactant composition into the hydrocarbon bearing formation at a temperature of from 100° C. to 120° C.*

61. *The method of claim 47, wherein the anionic ether sulfate surfactant formulation comprises the alkalinity generating agent in an amount such that the anionic ether sulfate surfactant is stable at 126° C.*

62. *The method of claim 47, wherein the anionic ether sulfate surfactant formulation has a pH of from about 10 to about 11.*

63. *The method of claim 46, wherein n is from 25 to 38.*

64. *The method of claim 46, wherein x is from greater than 20 to 50 and y is from greater than 20 to 100.*

65. *The method of claim 3, where y is a non-zero integer.*

66. *The composition of claim 30, where y is a non-zero integer.*

67. *The method of claim 13, wherein the alkalinity generating agent comprises $Na_2CO_3$.*

68. *The composition of claim 32, wherein the alkalinity generating agent comprises $Na_2CO_3$.*

69. *The method of claim 48, wherein the alkalinity generating agent comprises $Na_2CO_3$.*

\* \* \* \* \*